United States Patent
Liu et al.

(10) Patent No.: US 11,655,488 B1
(45) Date of Patent: May 23, 2023

(54) METHOD AND STRAINS FOR REDUCING BYPRODUCT SUCCINIC ACID IN FERMENTATION PROCESS OF L-MALIC ACID AND USE THEREOF

(71) Applicant: Nanjing Haohe Biotechnology Co., Ltd., Nanjing (CN)

(72) Inventors: Hao Liu, Nanjing (CN); Qing Xu, Nanjing (CN)

(73) Assignee: Nanjing Haohe Biotechnology Co., Ltd., Nanjing (CN)

( * ) Notice: Subject to any disclaimer, the term of this patent is extended or adjusted under 35 U.S.C. 154(b) by 0 days.

(21) Appl. No.: 17/744,778

(22) Filed: May 16, 2022

(30) Foreign Application Priority Data

Dec. 1, 2021 (CN) .......................... 202111445669.8

(51) Int. Cl.
| | |
|---|---|
| *C12P 7/46* | (2006.01) |
| *C12N 15/80* | (2006.01) |
| *C12N 9/00* | (2006.01) |
| *C07K 9/00* | (2006.01) |
| *C07K 14/38* | (2006.01) |
| *C12N 9/02* | (2006.01) |

(52) U.S. Cl.
CPC ................ *C12P 7/46* (2013.01); *C07K 14/38* (2013.01); *C12N 9/001* (2013.01); *C12N 15/80* (2013.01); *C12Y 103/00* (2013.01)

(58) Field of Classification Search
CPC ................................ C12N 15/80; C12N 9/001
See application file for complete search history.

(56) References Cited

FOREIGN PATENT DOCUMENTS

| | | |
|---|---|---|
| CN | 101240259 A | 8/2008 |
| CN | 102618570 A | 8/2012 |
| CN | 104046577 A | 9/2014 |
| CN | 111218408 A | 6/2020 |

*Primary Examiner* — Suzanne M Noakes

(57) ABSTRACT

The disclosure discloses an Aspergillus niger engineered strain for reducing byproduct succinic acid in a fermentation process of L-malic acid. The Aspergillus niger engineered strain is an Aspergillus niger engineered strain in which fumaric acid reductase frdA and fumaric acid reductase flavoprotein subunit frdB are simultaneously knocked out. The disclosure provides an frdA and frdB gene double-knockout Aspergillus niger strain, and a method for greatly reducing byproduct succinic acid in a fermentation process of L-malic acid. By the disclosure, the byproduct succinic acid accumulated in a production process of malic acid through fermentation of Aspergillus niger is significantly reduced, a cost in a downstream separation and purification process of malic acid is decreased, and good strains are provided for producing malic acid via industrial fermentation.

3 Claims, 14 Drawing Sheets

Specification includes a Sequence Listing.

FIG. 11

METHOD AND STRAINS FOR REDUCING BYPRODUCT SUCCINIC ACID IN FERMENTATION PROCESS OF L-MALIC ACID AND USE THEREOF

SEQUENCE LISTING

The instant application contains an electronic sequence listing that has been submitted in SCII format via EFS-Web and is hereby incorporated by reference in its entirety. The ASCII copy, created on 29 Jul. 2022, is named Sequence Listing.txt and is 26 kilobytes in size.

CROSS REFERENCE TO RELATED APPLICATIONS

This application claims foreign priority of Chinese Patent Application No. 202111445669.8, filed on Dec. 1, 2021 in the China National Intellectual Property Administration, the disclosures of all of which are hereby incorporated by reference.

TECHNICAL FIELD

The disclosure belongs to the technical field of biological engineering, particularly to a method and strains for reducing byproduct succinic acid in a fermentation process of L-malic acid, and use thereof.

BACKGROUD OF THE PRESENT INVENTION

L-malic acid, as an important organic acid, is widely present in plants, animals and microorganisms, is an important intermediate mesostate in a tricarboxylic acid cycle in an organism and widely applied to the fields of foods, medicines and chemical industry and the like. In food industry, malic acid combined with citric acid is broadly used as a food sour regulating agent due to natural fragrance of apples. In addition, malic acid can be used for food preservation and is combined with other preservatives, etc.; in medicine industry, malic acid is often used for treating abnormal liver functions and hyperammonemia because it can directly participate in metabolism of a human body, and is also often used in amino acid injection drugs to help the utilization of amino acids, etc.; in chemical industry, malic acid is ordinarily used for metal cleaning, printing and dyeing industry, non-electrolysis cladding layers, oil varnish and the like. Malic acid is initially extracted from fruits such as apples, and this method cannot satisfy the demand of a large-scale market due to limitation by contents, raw materials and other factors.

At present, industrialized production ways of malic acid mainly include a chemical synthesis method and a biological catalysis method. The chemical synthesis method uses petroleum base chemical benzene as a raw material to obtain racemic DL-malic acid under the conditions of high temperature and high pressure; as early as 1970, FDA banned DL-malic acid to be added in infant foods; in addition, the chemical synthesis method has high equipment requirements and fast equipment depreciation, which restricts its application in the fields of foods and medicines. Moreover, raw material sources of this method are petroleum base chemicals, which is a great challenge for increasingly decreasing petroleum energy and environment problems. The biological catalysis method is mainly an immobilized enzyme or immobilized cell transformation method. The immobilized enzyme method is high in extraction, purification and immobilization costs of an enzyme, and therefore causes revenues to be limited to a certain extent; the immobilized cell transformation method has the disadvantages that since living cells themselves contain a complicated enzyme system, many byproducts are easily formed, so as to increase the downstream purification cost of a product. In summary, malic acid prepared by the chemical synthesis method and the biological catalysis method difficultly satisfies an increasing demand on malic acid in the market.

Compared with the above two methods, a microbiological fermentation method pays more and more attentions because of its environmental friendliness, renewable carbon sources and the like. However, currently, this method has the defects of few safe strain selectivity, low product conversion rate or production efficiency, many heteroacid byproducts and high heteroacid byproduct content, which seriously restricts the industrialization progress for production of L-malic acid via a fermentation method.

By retrieval, patent public documents associated with this invention patent application have not yet been found so far.

SUMMARY OF PRESENT INVENTION

The objective of the disclosure is to provide a method and strains for reducing byproduct succinic acid in a fermentation process of L-malic acid and use thereof, in order to overcome the problems existing in the prior art.

The technical solution adopted by the disclosure to solve the technical problem is:

provided is an Aspergillus niger engineered strain for reducing byproduct succinic acid in a fermentation process of L-malic acid, wherein the Aspergillus niger engineered strain is an Aspergillus niger engineered strain in which fumaric acid reductase frdA and fumaric acid reductase flavoprotein subunit frdB are simultaneously knocked out.

Further, the gene sequence of the fumaric acid reductase gene frdA is SEQ NO:1, the amino acid sequence of the fumaric acid reductase gene frdA is SEQ NO:2, the gene sequence of the fumaric acid reductase flavoprotein subunit gene frdB is SEQ NO:5, and the amino acid sequence of the fumaric acid reductase flavoprotein subunit gene frdB is SEQ NO:6.

Further, the fumaric acid reductase gene frdA is NCBI-locus_tag ANI_1_944144, and the fumaric acid reductase flavoprotein subunit gene frdB is NCBI-locus_tag ANI_1_2554024.

Provided is a method for constructing the Aspergillus niger engineered strain for reducing byproduct succinic acid in a fermentation process of L-malic acid as described above, comprising the following steps:

(1) construction of a fumaric acid reductase gene frdA knockout Aspergillus niger engineered strain Step 1, constructing a gene frdA knockout vector:

respectively amplifying upstream and downstream sequence fragments of gene frdA through PCR reaction with a wild type Aspergillus niger ATCC1015 genome as a template, recovering PCR products to respectively obtain target fragments; and cloning the upstream and downstream sequence fragments of the gene frdA onto a vector pLH594, so as to construct a fumaric acid reductase frdA knockout vector pLH1067;

wherein the gene downstream sequence of the frdA gene is SEQ NO:3, and the upstream sequence of the frdA gene is SEQ NO: 4;

Step 2, obtaining of a frdA gene knockout strain:

transferring the vector pLH1-67 into Aspergillus niger S489 under the mediation of Agrobacterium, and conducting transformant screening and hygromycin resistance gene recombination to obtain a frdA gene knockout strain K1.

(2) construction of an fumaric acid reductase gene frdA and fumaric acid reductase flavoprotein subunit gene frdB double-knockout Aspergillus niger engineered strain Step 1, constructing a gene frdB knockout vector:

respectively amplifying upstream and downstream sequence fragments of gene frdB through PCR reaction with a wild type Aspergillus niger ATCC1015 genome as a template, recovering PCR products to respectively obtain target fragments; and cloning the upstream and downstream sequence fragments of the gene frdB onto a vector pLH594, so as to construct a fumaric acid reductase flavoprotein subunit frdB knockout vector pLH1162;

wherein the downstream sequence of the frdB gene is SEQ NO:7, and the upstream sequence of the frdB gene is SEQ NO: 8;

Step 2, obtaining of a frdA gene and frdB gene double-knockout strain:

transferring the vector pLH1162 into the frdA gene knockout strain K1 under the mediation of Agrobacterium, and conducting transformant screening and hygromycin resistance gene recombination to obtain a frdA gene and frdB gene double-knockout strain K2, that is, an Aspergillus niger engineered strain for reducing byproduct succinic acid accumulation in a fermentation process of L-malic acid.

Provided is a method for fermenting L-malic acid by utilizing the Aspergillus niger engineered strain as described above, comprising the following steps:

inoculating the Aspergillus niger engineered strain into a PDA culture medium to be cultured for 5 days at 28° C. until conidia are generated, collecting the conidia and inoculating a conidium suspension into a fermentation culture medium, wherein the concentration of the conidia is $1*10^8$ conidia/50 ml, and then culturing for 5 days at 28° C. in a constant-temperature shaker at 200 rpm to obtain L-malic acid.

Further, components and a formulation method of a malic acid fermentation culture medium are as follows:

the components and the formulation method of the malic acid fermentation culture medium: 100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid, a solvent is water, and autoclaving is performed for 20 min at 115° C.

Further, the yield of the L-malic acid obtained by the method is 65.59-69.15 g/L which is increased by 7.92% compared with that of a starting strain, and the yield of succinic acid is 0.91-1.05 g/L which is reduced by 88.73% compared with that of the starting strain.

Provided is use of the Aspergillus niger engineered strain as described above in production of L-malic acid.

The disclosure has the beneficial effects:

The disclosure overcomes the defects in the prior art, in the current production process of malic acid through fermentation of Aspergillus niger, the byproduct succinic acid is accumulated with the generation of malic acid so as to cause the improved cost of the subsequent malic acid purification process, and the disclosure provides an frdA and frdB gene double-knockout Aspergillus niger strain and a method for greatly reducing byproduct succinic acid in a fermentation process of Aspergillus niger. By the disclosure, the byproduct succinic acid accumulated in the production process of L-malic acid through fermentation of Aspergillus niger is greatly reduced, the cost in the process of downstream separation and purification of malic acid is decreased, and good strains are provided for industrial fermentation and production of malic acid.

2. The Aspergillus niger strain of the disclosure can be applied to production of L-malic acid, after this strain is fermented for 5 days under the condition of a shaker, the yield of L-malic acid is 65.59-69.15 g/L which is improved by 7.92% compared with that of the starting strain, and the content of succinic acid is 0.91-1.05 g/L which is reduced by 88.73% compared with that of the starting strain. Good strains are provided for preparing malic acid using the microbiological fermentation method.

3. The starting strain used in the disclosure is the previously constructed Aspergillus niger S489 (for producing malic acid in high yield), the Aspergillus niger engineered strain is an Aspergillus niger strain in which the fumaric acid reductase gene frdA and the fumaric acid reductase flavoprotein subunit gene frdB are simultaneously knocked out on the basis of S489.

DESCRIPTION OF THE DRAWINGS

FIG. 11 is a comparison diagram of similarities between frdA (SEQ ID NO: 2) and frdB protein sequences (SEQ ID NO: 6) in the disclosure;

DETAILED DESCRIPTION OF PREFERRED EMBODIMENTS

Figure 1:
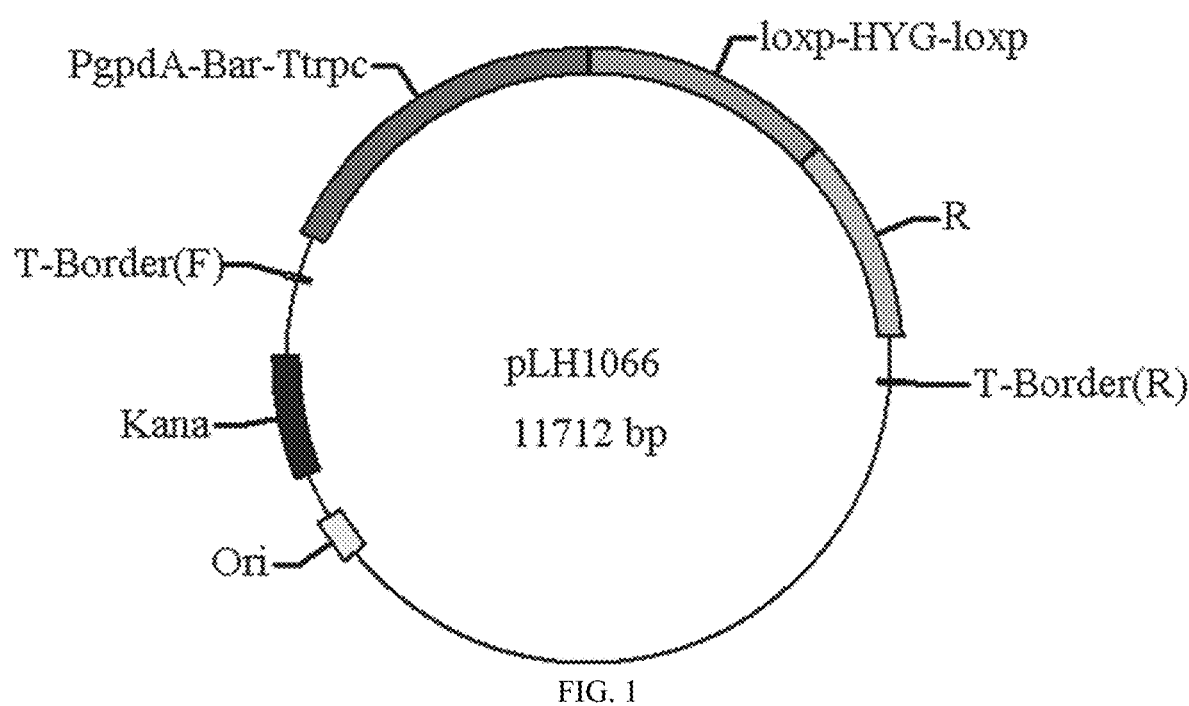
FIG. 1 is a map of a vector pLH1066 constructed in the disclosure for knocking out an frdA gene linked homologous right arm.

To better understand the disclosure, the disclosure will be further described in detail in combination with embodiments. However, the scope claimed by the disclosure is not limited to the scope represented by embodiments.

Raw materials used in the disclosure, unless otherwise noted, are all conventional commercially available products. The methods used in the disclosure, unless otherwise noted, are all conventional methods in the art. The masses of various substances used in the disclosure are conventional use masses.

An Aspergillus niger engineered strain for reducing byproduct succinic acid in a fermentation process of L-malic acid is an Aspergillus niger engineered strain in which fumaric acid reductase frdA and fumaric acid reductase flavoprotein subunit frdB are simultaneously knocked out.

Preferably, the gene sequence of the fumaric acid reductase gene frdA is SEQ NO:1, the amino acid sequence of the fumaric acid reductase gene frdA is SEQ NO:2, the gene sequence of the fumaric acid reductase flavoprotein subunit gene frdB is SEQ NO:5, and the amino acid sequence of the fumaric acid reductase flavoprotein subunit gene frdB is SEQ NO:6.

Preferably, the fumaric acid reductase gene frdA is NCBI-locus_tag ANI_1_944144, and the fumaric acid reductase flavoprotein subunit gene frdB is NCBI-locus_tag ANI_1_2554024.

A method for constructing the Aspergillus niger engineered strain for reducing byproduct succinic acid in a fermentation process of L-malic acid as described above comprises the following steps:

(1) construction of a fumaric acid reductase gene frdA knockout Aspergillus niger engineered strain Step 1, constructing a gene frdA knockout vector:

respectively amplifying upstream and downstream sequence fragments of gene frdA through PCR reaction with a wild type Aspergillus niger ATCC1015 genome as a template, recovering PCR products to respectively obtain target fragments; and cloning the upstream and downstream sequence fragments of the gene frdA onto a vector pLH594, so as to construct a fumaric acid reductase frdA knockout vector pLH1067;

wherein the downstream sequence of the frdA gene is SEQ NO:3, the upstream sequence of the frdA gene is SEQ NO: 4;

Step 2, obtaining of an frdA gene knockout strain:

transferring the vector pLH1-67 into an Aspergillus niger S489 (a previously constructed malic acid high-yield strain, as described in Xu, Y., Shan, L., Zhou, Y. et al. Development of a Cre-loxP-based genetic system in Aspergill usniger ATCC1 01 5 and its application to construction of efficient organic acid-producing cell factories. Appl Microbiol Biotechnol 103, 8105-8114 (2019). doi .org/10 .1007/s00253-019-10054-3) under the mediation of Agrobacterium, and conducting transformant screening and hygromycin resistance gene recombination to obtain an frd A gene knockout strain K1;

(2) construction of a fumaric acid reductase gene frdA and fumaric acid reductase flavoprotein subunit gene frdB double-knockout Aspergillus niger engineered strain Step 1, constructing a gene frdB knockout vector:

respectively amplifying upstream and downstream sequence fragments of gene frdB through PCR reaction with a wild type Aspergillus niger ATCC1015 genome as a template, recovering PCR products to respectively obtain target fragments; and cloning the upstream and downstream sequence fragments of the gene frdB onto a vector pLH594, so as to construct a fumaric acid reductase flavoprotein subunit frdB knockout vector pLH1162;

wherein the downstream sequence of the frdB gene is SEQ NO:7, and the upstream sequence of the frdB gene is SEQ NO: 8;

Step 2, obtaining of an frdA and frdB gene double-knockout strain:

transferring the vector pLH1162 into the frdA gene knockout strain K1 under the mediation of Agrobacterium, and conducting transformant screening and hygromycin resistance gene recombination to obtain an frd A gene and frdB gene dual-knockout strain K2, that is, the Aspergillus niger engineered strain for reducing byproduct succinic acid accumulation in a fermentation process of L-malic acid.

A method for fermenting L-malic acid by utilizing the Aspergillus niger engineered strain as described above comprises the following steps:

inoculating the Aspergillus niger engineered strain into a PDA culture medium to be cultured for 5 days at 28° C. until conidia are generated, collecting the conidia and inoculating a conidium suspension into a fermentation culture medium, wherein the concentration of the conidia is $1*10^8$ conidia/50 ml, and then culturing for 5 days at 28° C. in a constant-temperature shaker at 200 rpm to obtain L-malic acid.

Preferably, components and a formulation method of a malic acid fermentation culture medium are as follows:

the components and a formulation method of a malic acid fermentation culture medium: 100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid, a solvent is water, and autoclaving is performed for 20 min at 115° C.

Preferably, the yield of the L-malic acid obtained by the method is 65.59-69.15 g/L which is increased by 7.92% compared with a staring strain, and the yield of succinic acid is 0.91-1.05 g/L which is reduced by 88.73% compared with the starting strain.

Provided is use of the Aspergillus niger engineered strain as described above in production of L-malic acid.

Specifically, relevant preparation and detection are as follows:

Example 1: construction of an frd A gene and frdB gene knockout vector

This example includes the following steps:

(1) construction of a frdA gene knockout vector

Figure 2:
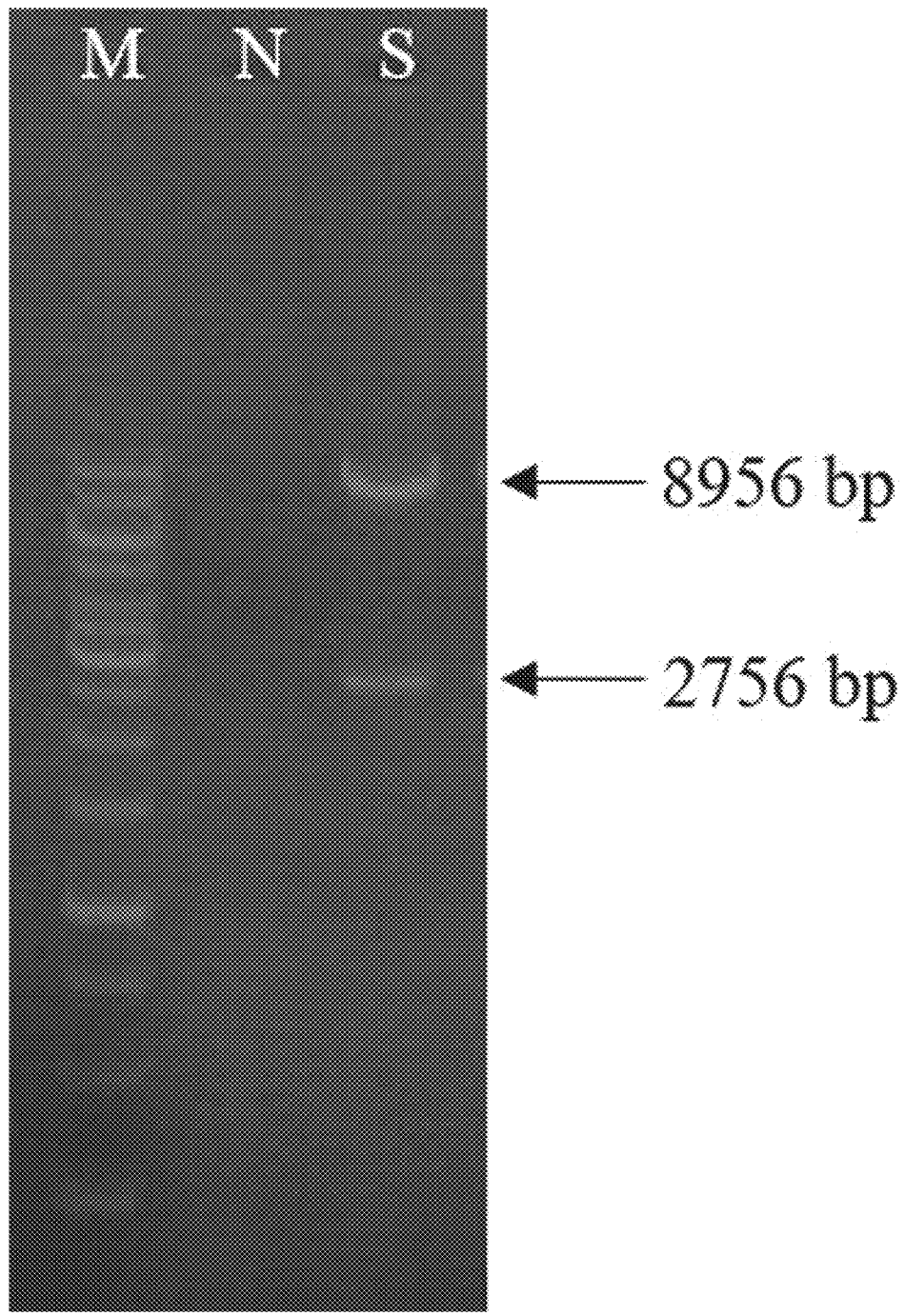
FIG. 2 is a double digestion validation diagram of a knockout vector pLH1066 in the disclosure; wherein, M is DNA Marker, N is negative control, and S is a Sac I and Spe I double digestion validation vector.

To amplify the downstream sequence fragment of the frdA gene, an Aspergillus niger ATCC1015 genome was used as a template to design amplification primers frdA-F-F and frdA-F-R, the downstream sequence fragment of the frdA gene was recovered by PCR amplification, subjected to Xba I and Spe I double digestion and glue recovery and then linked to a vector pLH594 obtained by the same restriction enzyme by virtue of One-Step Clone Kit, the linked product was transformed into E. coli JM109 competent cells and then evenly coated in an LB solid culture medium containing 100 μg/mL kanamycin resistance and inverted overnight at 37° C., and monoclones were picked to be subjected to colony PCR validation and plasmid double-digestion validation (FIG. 2) so as to obtain a vector pLH1066 successfully linked to the downstream sequence fragment of the frdA gene, whose map is shown in FIG. 1.

Figure 3:
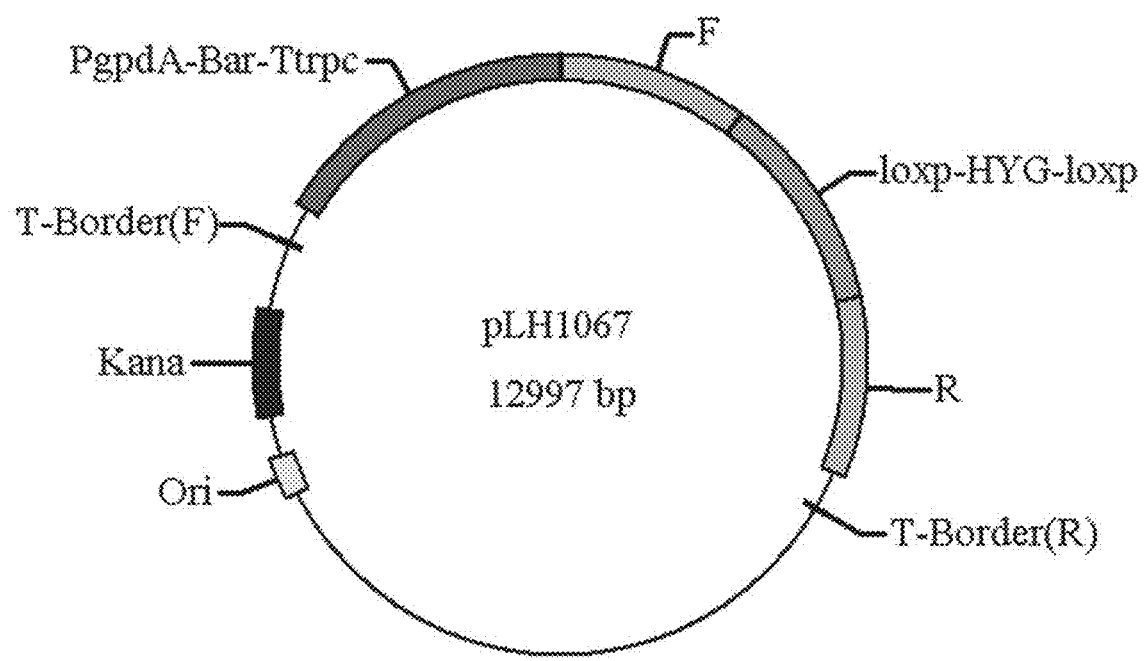
FIG. 3 is a map of a vector pLH1067 constructed in the disclosure for knocking out frdA gene linked homologous left and right arms.
Figure 4:
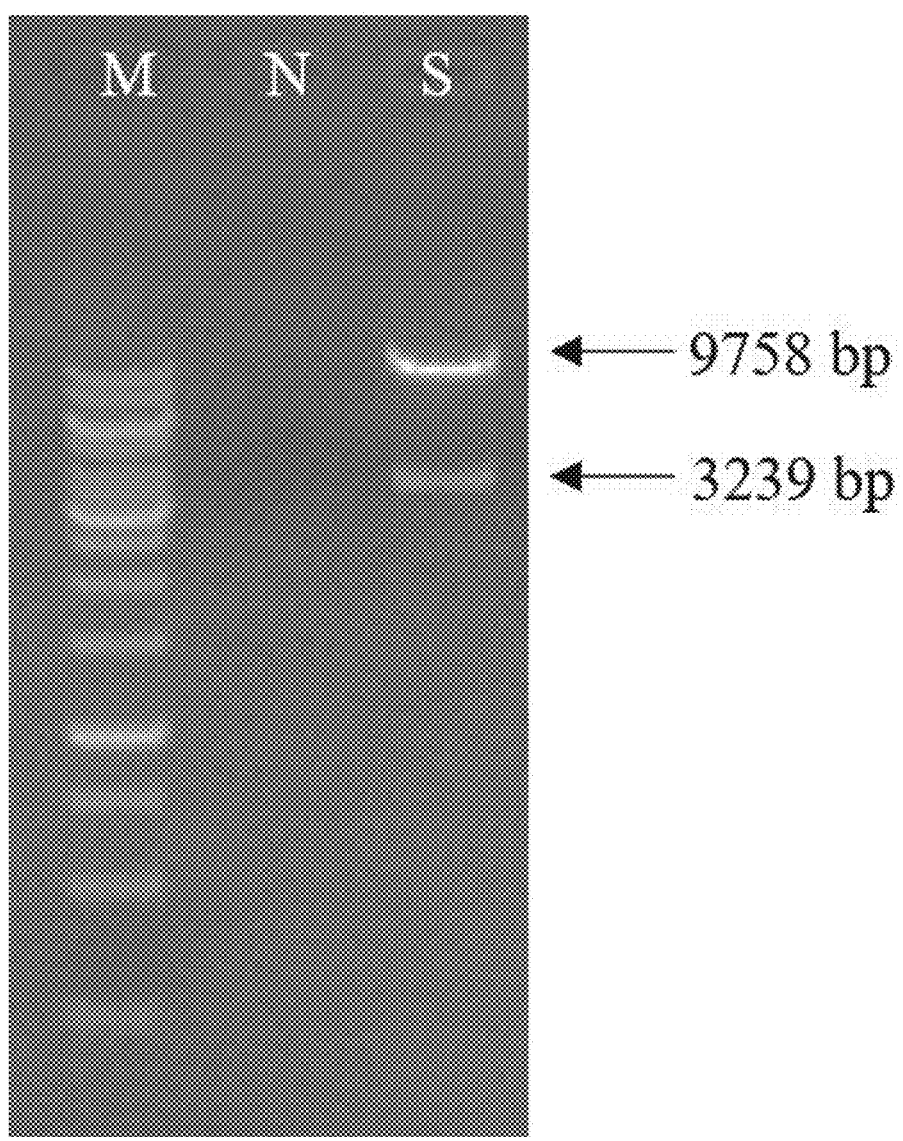
FIG. 4 is a double digestion validation diagram of a knockout vector pLH1067 in the disclosure; wherein, M is DNA Marker, N is negative control, and S is Spe I restriction enzyme digestion validation vector.

To amplify the upstream sequence fragment of the frdA gene, an Aspergillus niger genome was used as a template to design amplification primers frdA-R-F and frdA-R-R, the upstream sequence fragment of the frdA gene was recovered by PCR amplification, subjected to Sac I and BamH I double digestion and glue recovery and then linked to a vector pLH1066 obtained by the same restriction enzyme by virtue of One-Step Clone Kit, the linked product was transformed into E. coli JM109 competent cells and then evenly coated in an LB solid culture medium containing 100 μg/mL kanamycin resistance and inverted overnight at 37° C., and monoclones were picked to be subjected to colony PCR validation and plasmid double-digestion validation (FIG. 4) so as to obtain vector pLH1067 successfully linked to the upstream sequence fragment of the frd A gene, whose spectrum is shown in FIG. 3.

Amplification primers are seen in Table 1, and are identified as SEQ ID Nos: 9-26, respectively.

TABLE 1

Primer sequence

| SEQ ID NOs | Primer name | Primer sequence (5'-3') |
| --- | --- | --- |
| 9 | frdA-F-F | CCCAGAATTCAATTCGAGCTCCAGGTGACGTGGGAAGGATC |
| 10 | frdA-F-R | ATTATACGAAGTTATGGATCCGAGGGAAGGGAGACAAGGATG |
| 11 | frdA-R-F | GCTATACGAAGTTATTCTAGAGCCTAGAGCTGTAAAAACCCCG |
| 12 | frdA-R-R | TGCCTGCAGGGGCCCACTAGTACTTCTGCCTCTCCCTCGAC |
| 13 | frdB-F-F | GCTCCGTAACACCCAGAATTCGTGCACCTTTCACCGTCCTG |
| 14 | frdB-F-R | CGAAGTTATGGATCCGAGCTCGTTACCTCCTGCCCATTCCTCC |
| 15 | frdB-R-F | GCTATACGAAGTTATTCTAGAGACCACACTGGGACGTGG |
| 16 | frdB-R-R | TGCCTGCAGGGGCCCACTAGTAGACTACAACCGTGCCTGC |
| 17 | P1 | CACGGCATGCTAATTGGTG |
| 18 | P2 | GATCAACTCACGTCCACCG |
| 19 | P3 | GCGATGCCACAGAAGGTATG |
| 20 | P4 | TCGGGCCTTGCAAAGAATG |
| 21 | P5 | CCAGGATGTGTTGGCGACG |
| 22 | P6 | TGGACGGTGCGCATTGCC |
| 23 | P7 | GAACCCGCGCATGCGCGC |
| 24 | P8 | GACATAGTATATTATTCCTGC |
| 25 | P641 | CAATATCAGTTAACGTCGAC |
| 26 | P642 | GGAACCAGTTAACGTCGAAT | a Underline sequence represents restriction enzyme sites

Figure 5:
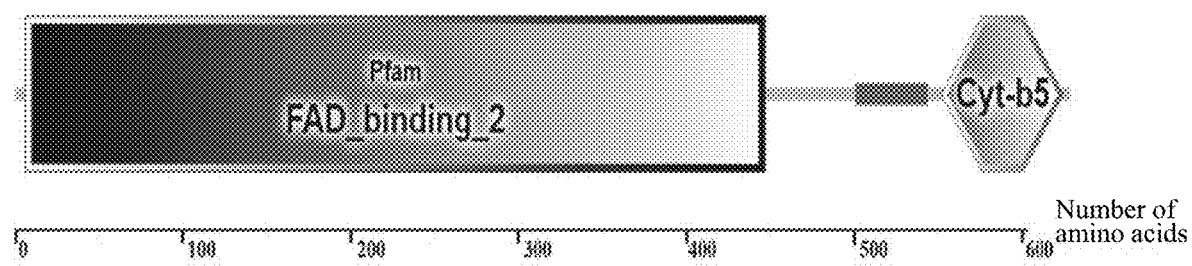
FIG. 5 shows a protein domain of a knockout gene frdA in the disclosure.

The gene sequence of the gene frdA is SEQ NO:1, with a length of 2496 bp; the amino acid sequence of the gene frdA is SEQ NO:2, with 629 amino acids; the functional domain of a protein is shown in FIG. 5.

The downstream sequence of the frdA gene is SEQ NO:3, with a length of 1245 bp;

The upstream sequence of the frdA gene is SEQ NO:4, with a length of 1285 bp;

The LB solid culture medium containing kanamycin resistance comprises the following components: 10 g/L of tryptone, 5 g/L of yeast extract, 10 g/L of sodium chloride and 15 g/L of agar powder. Sterilization was performed for 20 min at 121° C. Kanamycin was added when sterilizing and cooling to about 50° C. until a final concentration was 100 μg/mL.

(2) Construction of an frdB gene knockout vector

Figure 6:
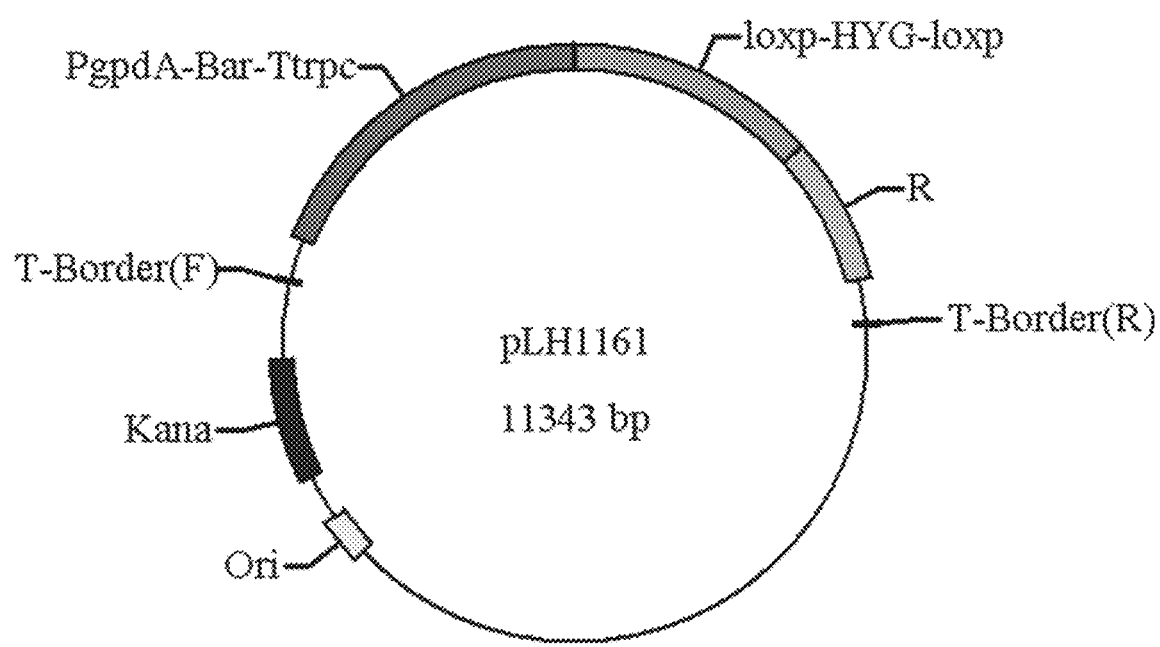
FIG. 6 is a map of a vector pLH1161 constructed in the disclosure for knocking out an frdB gene linked homologous right arm.
Figure 7:
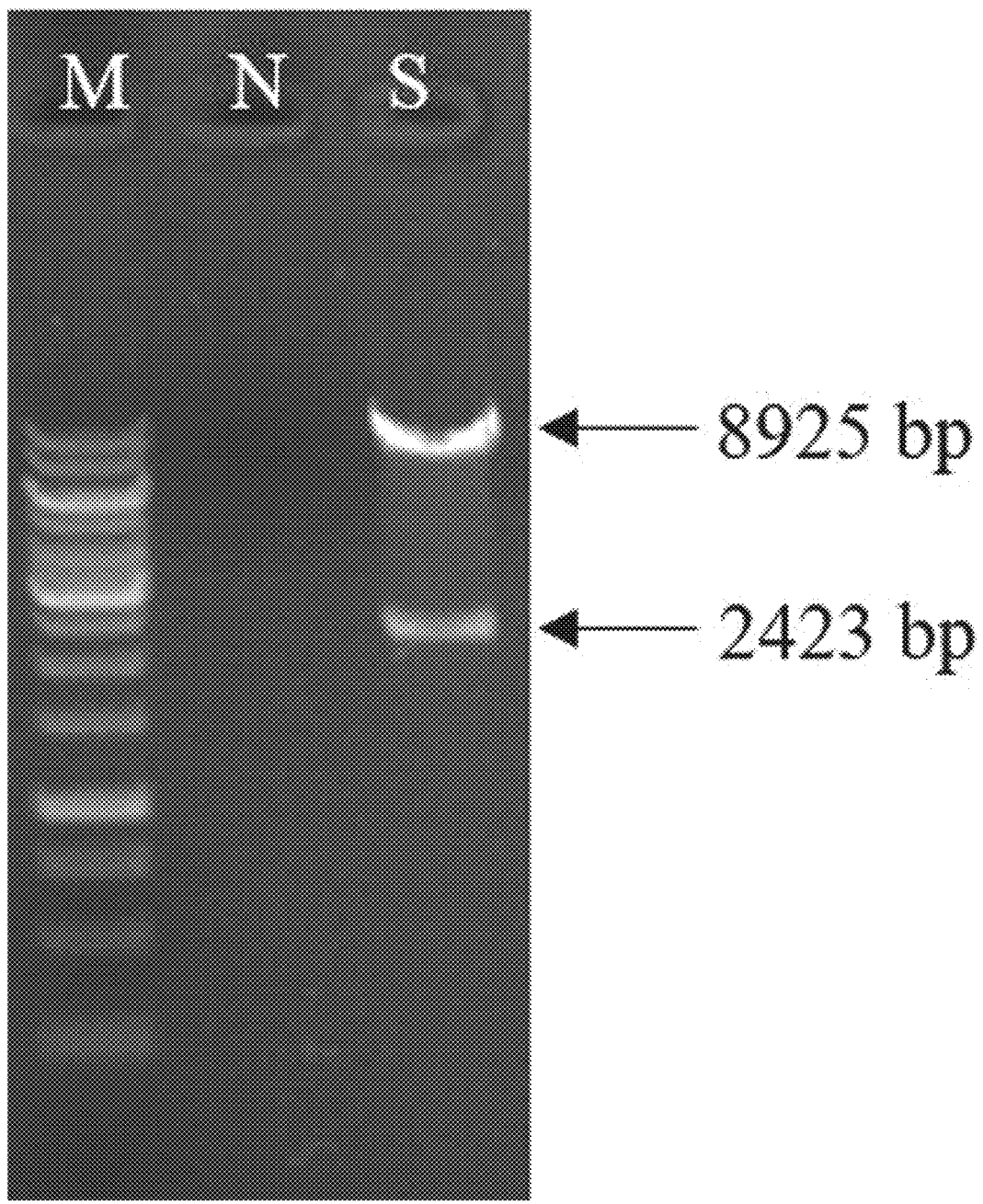
FIG. 7 is a double digestion validation diagram of a knockout vector pLH1161 in the disclosure; wherein, M is DNA Marker, N is negative control, and S is an EcoRI and Pst I digestion validation vector.

To amplify the downstream sequence fragment of a frdB gene, an Aspergillus niger ATCC1015 genome was used as a template to design amplification primers frdB-F-F and frdB-F-R, the downstream sequence fragment of the frdB gene was recovered by PCR amplification, subjected to Xba I and Spe I double digestion and glue recovery and then linked to a vector pLH594 obtained by the same restriction enzyme by virtue of One-Step Clone Kit, the linked product was transformed into E. coli JM109 competent cells and then evenly coated in an LB solid culture medium containing 100 μg/mL kanamycin resistance and inverted overnight at 37° C., and monoclones were picked to be subjected to colony PCR validation and plasmid double-digestion validation (FIG. 7), so as to obtain a vector pLH1161 successfully linked to the downstream sequence fragment of the frdBgene, whose map is shown in FIG. 6.

Figure 8:
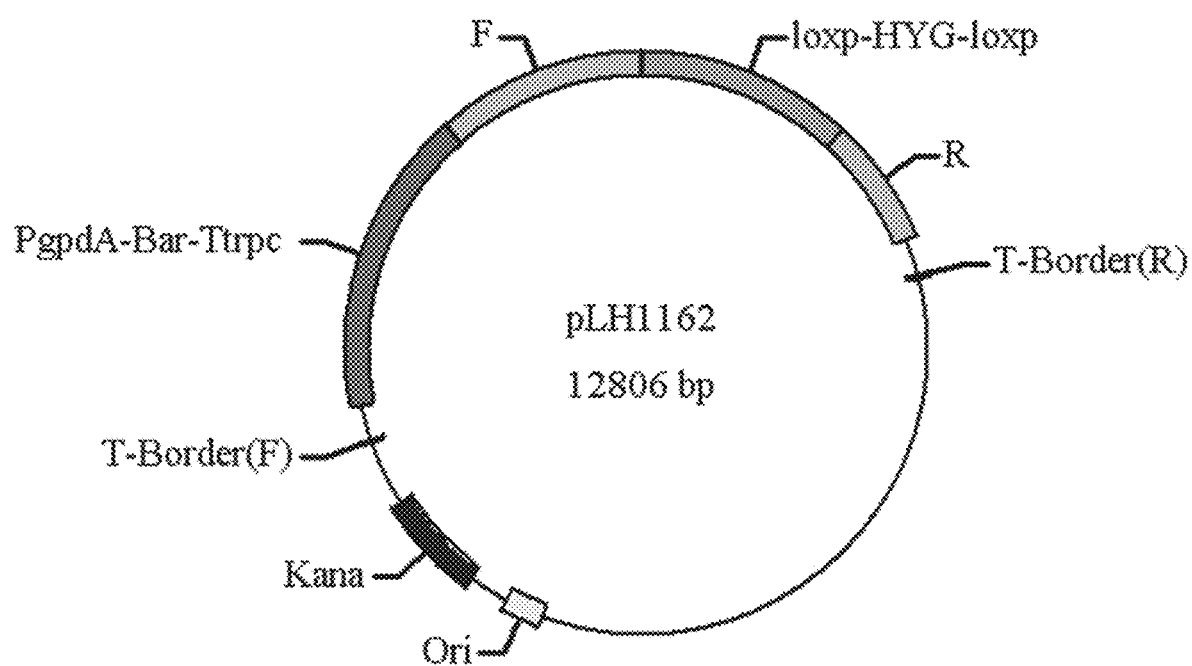
FIG. 8 is a map of a vector pLH1162 constructed in the disclosure for knocking out frdB gene homologous left and right arms.
Figure 9:
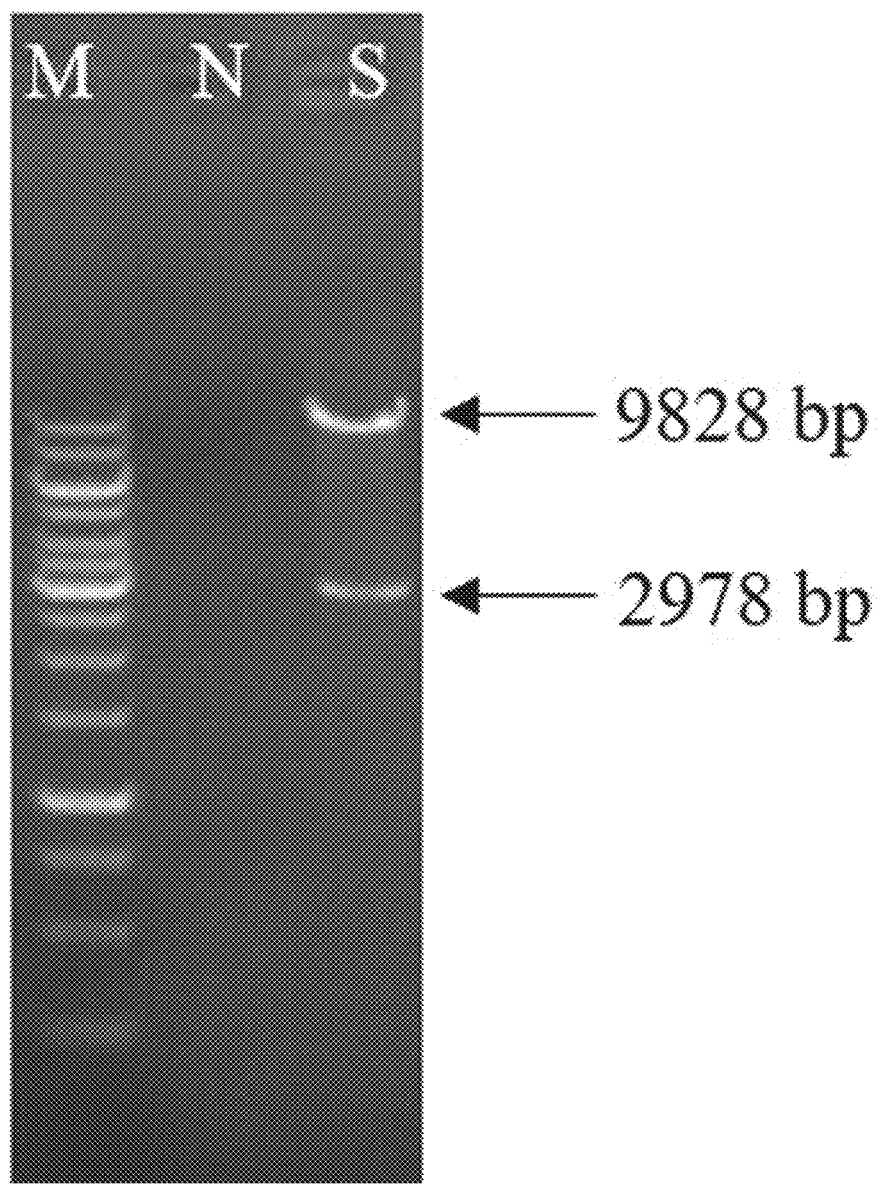
FIG. 9 is a double digestion validation diagram of a knockout vector pLH1162 in the disclosure; wherein, M is DNA Marker, N is negative control, and S is an EcoRI and Xba I digestion validation vector.

To amplify the upstream sequence fragment of the frdB gene, an Aspergillus niger genome was used as a template to design amplification primers frdB-R-F and frdB-R-R, the upstream sequence fragment of the frdB gene was recovered by PCR amplification, subjected to EcoR I and Sac I double digestion and glue recovery and then linked to a vector pLH1161 obtained by the same restriction enzyme by virtue of One-Step Clone Kit, the linked product was converted into E. coli JM109 competent cells and then evenly coated in an LB solid culture medium containing 100 μg/mL kanamycin resistance and inverted overnight at 37° C., and monoclones were picked to be subjected to colony PCR validation and plasmid double-digestion validation (FIG. 9), so as to obtain a vector pLH1162 successfully linked to the upstream sequence fragment of the frdB gene, whose map is shown in FIG. 8.

Amplification primers are seen in Table 1.

Figure 10:
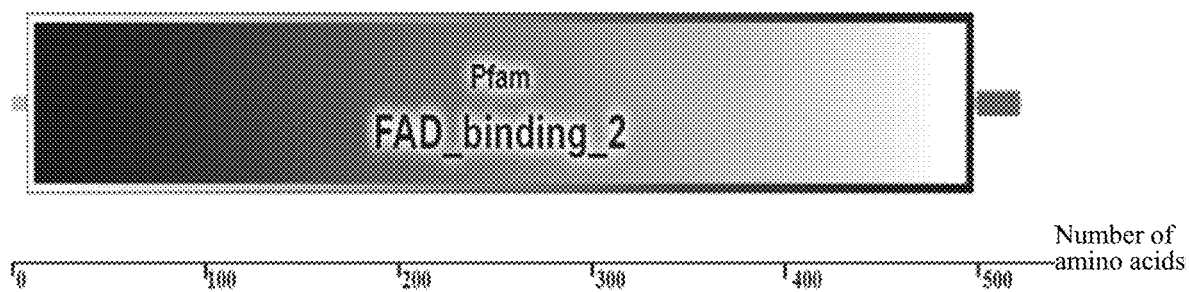
FIG. 10 shows a protein domain of a knockout gene frdB in the disclosure.

The gene sequence of the gene frdB is SEQ NO:5, with a length of 1569 bp; the amino acid sequence of the the gene frdB is SEQ NO:6, with 522 amino acids; the functional domain of a protein is shown in FIG. 10.

The downstream sequence of the frdB gene is SEQ NO:7, with a length of 881 bp;

The upstream sequence of the frdB gene is SEQ NO:8, with a length of 1463 bp.

Figure 11:
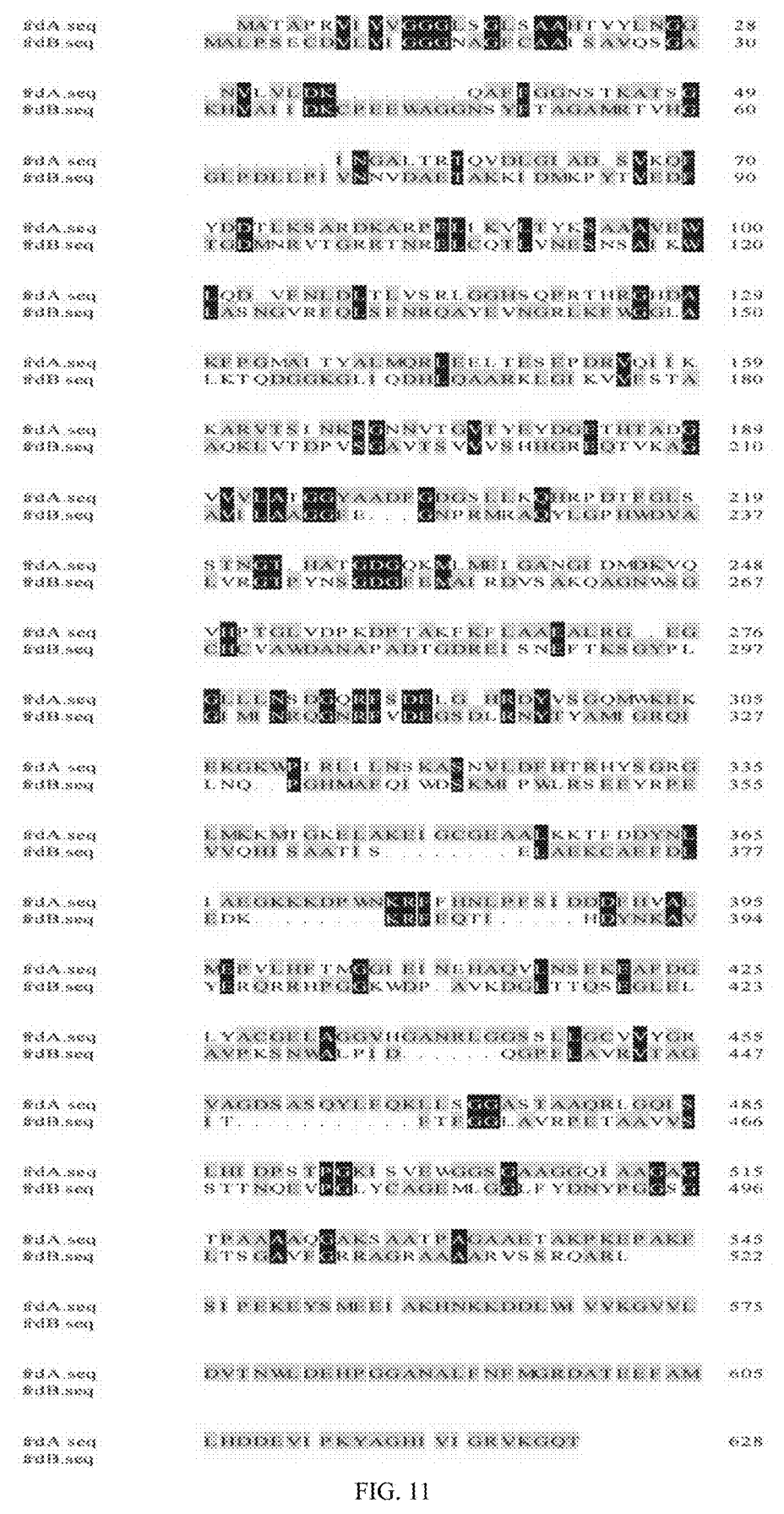

The comparison results of similarities between frdA and frdB protein sequences are shown in FIG. 11.

Example 2: obtaining of an Aspergillus niger gene knockout strain

This example is achieved through the following steps:

(1) construction of a frdA gene knockout strain K1

Figure 12:
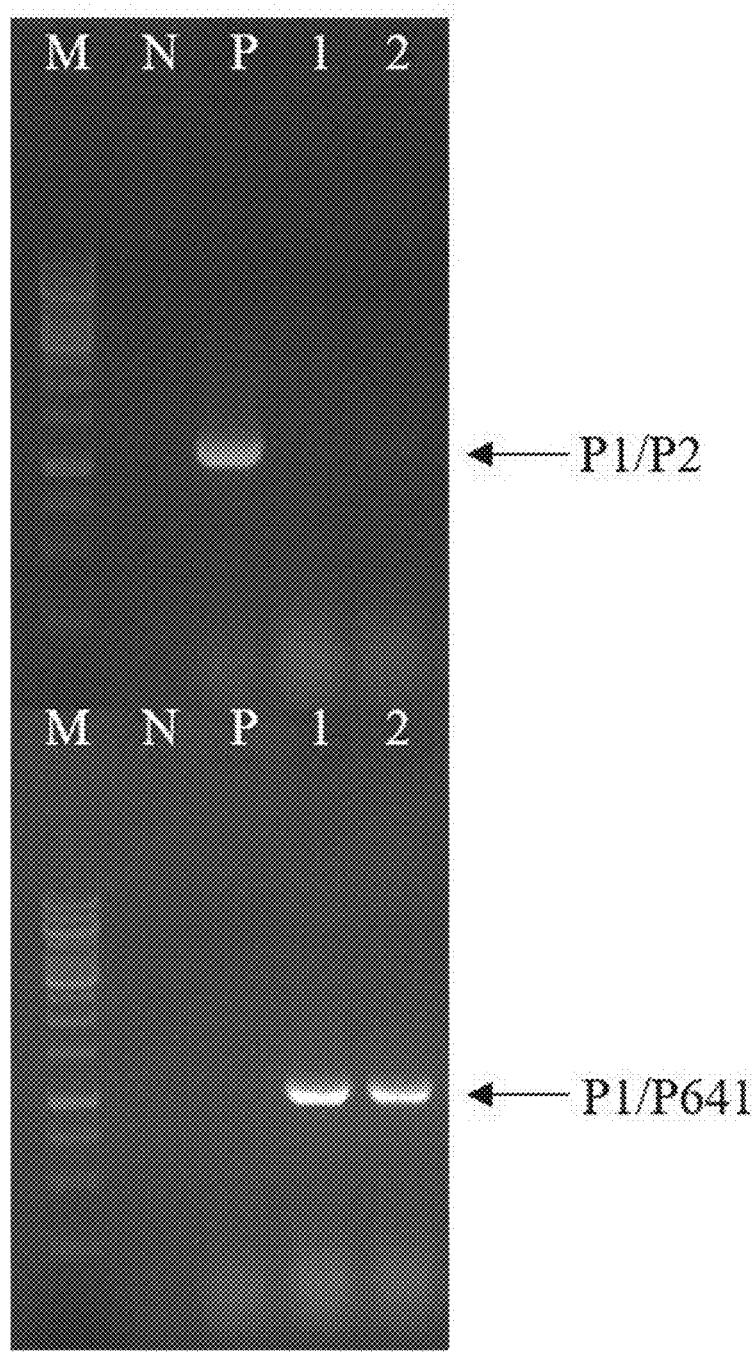
FIG. 12 is a PCR validation diagram of a frdA gene knockout left homology arm in the disclosure, primers P1 and P2 verify a left homology arm, and primers P1 and P641 verify a left homology arm-php; wherein, M is DNA Marker, N is Negative control, P is positive control, and 1-2 is an Aspergillus niger transformant genome in which a frdA gene is successfully knocked out.
Figure 13:
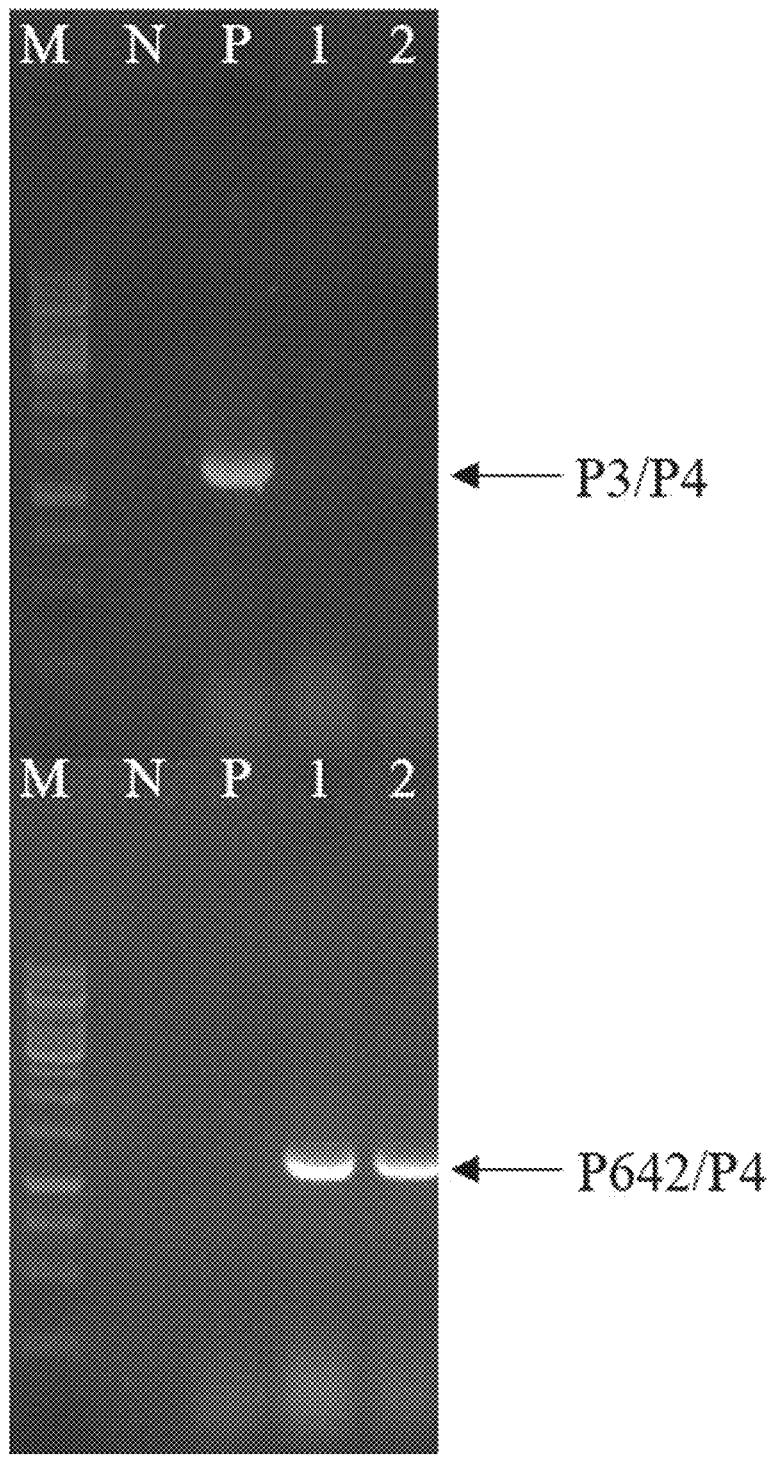
FIG. 13 is a PCR validation diagram of a frdA gene knockout right homology arm in the disclosure, primers P3 and P4 verify a right homology arm, and primers P642 and P4 verify a right homology arm-php; wherein, M is DNA Marker, N is Negative control, P is a positive control, and 1-2 is an Aspergillus niger transformant genome in which a frdA gene is successfully knocked out.

The vector pLH1067 was electroporated into agrobacterium, then this agrobacterium and an Aspergillus niger host strain S489 were co-cultured in an IM culture medium for agrobacterium-mediated transformation, the culture product was evenly coated in a CM culture medium after culturing for 2.5 days to be cultured until transformants were grown, and then the transformants were transferred to different culture mediums to be screened. The phenotypes of the transformants on different culture mediums should have resistance to hygromycin and sensitivity to glufosinate-ammonium. Such the transformants were subjected to genome validation and validation primers were designed (Table 1). Amplification results satisfy that the amplification of left and right homology arms is negative (FIG. 12 (P1/P2) FIG. 13 (P3/P4)), and the amplification of left and right homology arms-php is positive (FIG. 12 (P1/P641) FIG. 13 (P642/P4)), and one of the correct frdA knockout clones was picked for induction and recombination of resistance marker hygromycin, so as to obtain a frdA knockout strain K1 without hygromycin resistance.

The transformation method of the gene knockout is an agrobacterium-mediated method.

The electrotransformation conditions of the agrobacterium-mediated method are as follows: Capacitnce: 25 uF, Voltage: 2 .5 kV, Resistance: 200 Ω, Pulse: 5 msec.

The agrobacterium strain is an AGL-1 strain.

A method for formulating the IM culture medium comprises: water was added into 15 g of agar so that a 905.7 mL volume was reached, sterilization was performed at 121° C. for 20 min, 0.8 mL of sterile K buffer, 20 mL of MN buffer, 1 mL of 1% $CaCl_2 \cdot 2H_2O$, 10 mL of 0.01% $FeSO_4$, 5 mL of IM Trace elements, 2 .5 mL of 20% $NH_4NO_3$, 10 mL of 50% glycerol, 40 mL of 1M MES and 5 mL of 20% glucose which were prepared in advance were added, kanamycin was added when the temperature was reduced to about 50° C. so that a final concentration was 100 μg/mL, acetosyringone was added so that the final concentration was 200 μM.

A method for formulating the CM culture medium comprises: water was added into 20 g of agar so that a 897 mL volume was reached, sterilization was performed at 121° C. for 20 min, 20 mL of aseptic ASP+N, 20 mL of 50% glucose, 2 mL of 1M $MgSO_4$, 1 mL of CM Trace elements, 10 mL of 10% casein hydrolyzate and 50 mL of 10% yeast extract which were prepared in advance were added, hygromycin was added when the temperature was reduced to about 50° C. so that the final concentration was 250 μg/mL, streptomycin was added so that the final concentration was 100 μg/mL, cefotaxime sodium was added so that the final concentration was 100 μg/mL, and ampicillin was added so that the final concentration was 100 μg/mL.

The validation primer sequences are seen in Table 1.

The induction and recombination method of the resistance marker comprises: spores of about 400 frdA gene knockout clones were evenly coated onto an MM culture medium containing 30 μg/mL tetracycline, cultured at 28° C. until monoclones were grown, and 100 monoclones were randomly picked and transferred to a PDA culture medium to be cultivated at 28° C. for 24 h, and then the clones were transferred to a PDA medium containing hygromycin for 24 h at 28° C. one by one, and finally the phenotypes were observed to screen the transformants induced and recombined by resistance markers, that is, the transformants which can be normally grown in the PDA culture medium but cannot be normally grown in the PDA culture medium containing hygromycin were successfully induced and recombined transformants.

A method for formulating the PDA culture medium comprises: 200 g of peeled potatoes were accurately weighed and cut into about 1 $cm^3$ of small pieces, distilled water was added, the resulting mixture was boiled for 30 min under the condition of continuous stirring and filtered with double-layer gauze, filtrate was collected, 20 g of glucose was stirred until it was completely dissolved, the volume was adjusted to 1 L with distilled water, the resulting mixture was packaged into a jar, 1.5% agar was added, and the jar was autoclaved at 121° C. for 20 min.

(2) Construction of a frdB gene knockout strain K2

Figure 14:
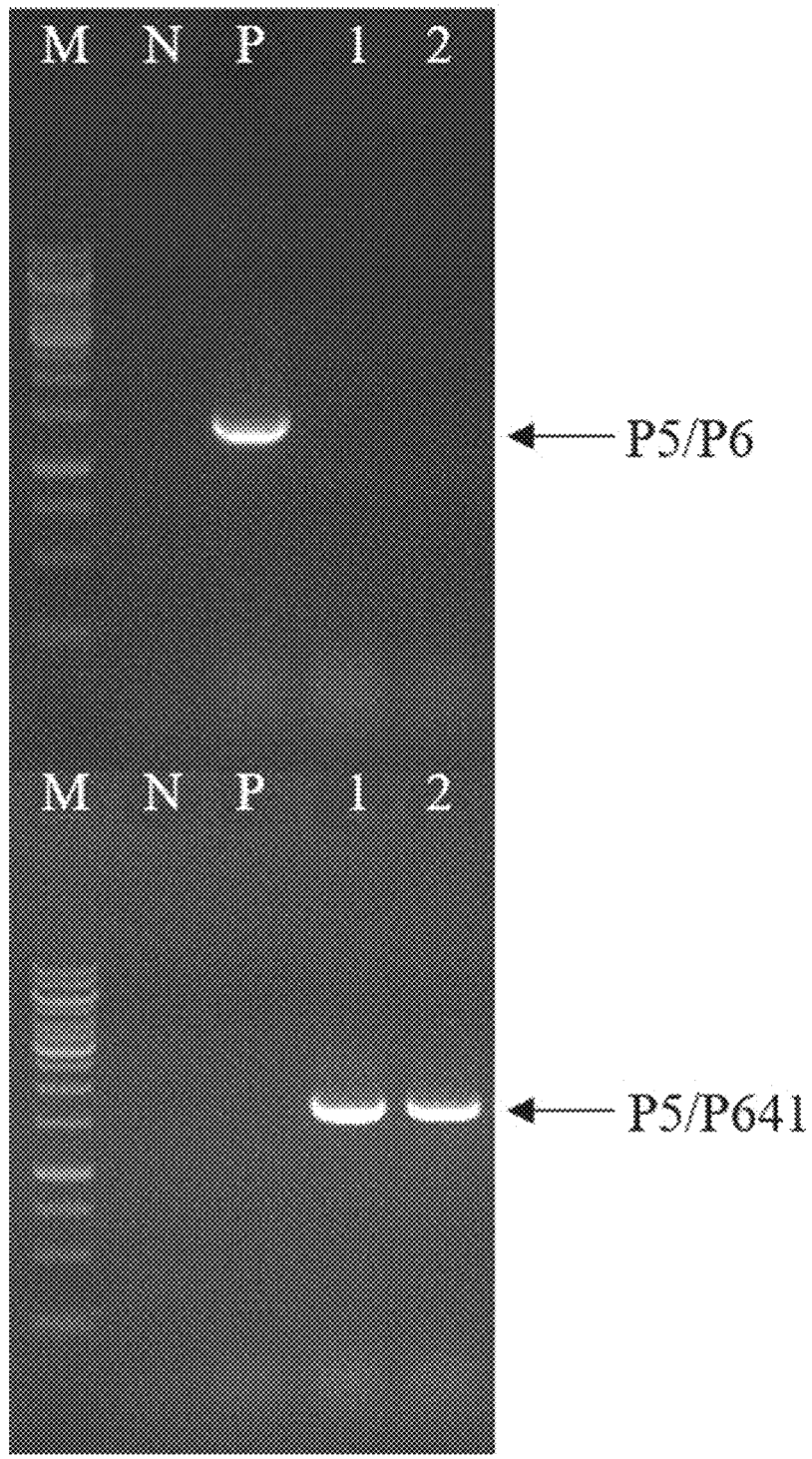
FIG. 14 is a PCR validation diagram of a frdB gene knockout left homology arm in the disclosure, primers P5 and P6 verify a left homology arm, and primers P6 and P641 verify a left homology arm-php; wherein, M is DNA Marker, and N is negative control, P is a positive control, and 1-2 is an Aspergillus niger transformant genome in which a frdB gene is successfully knocked out.
Figure 15:
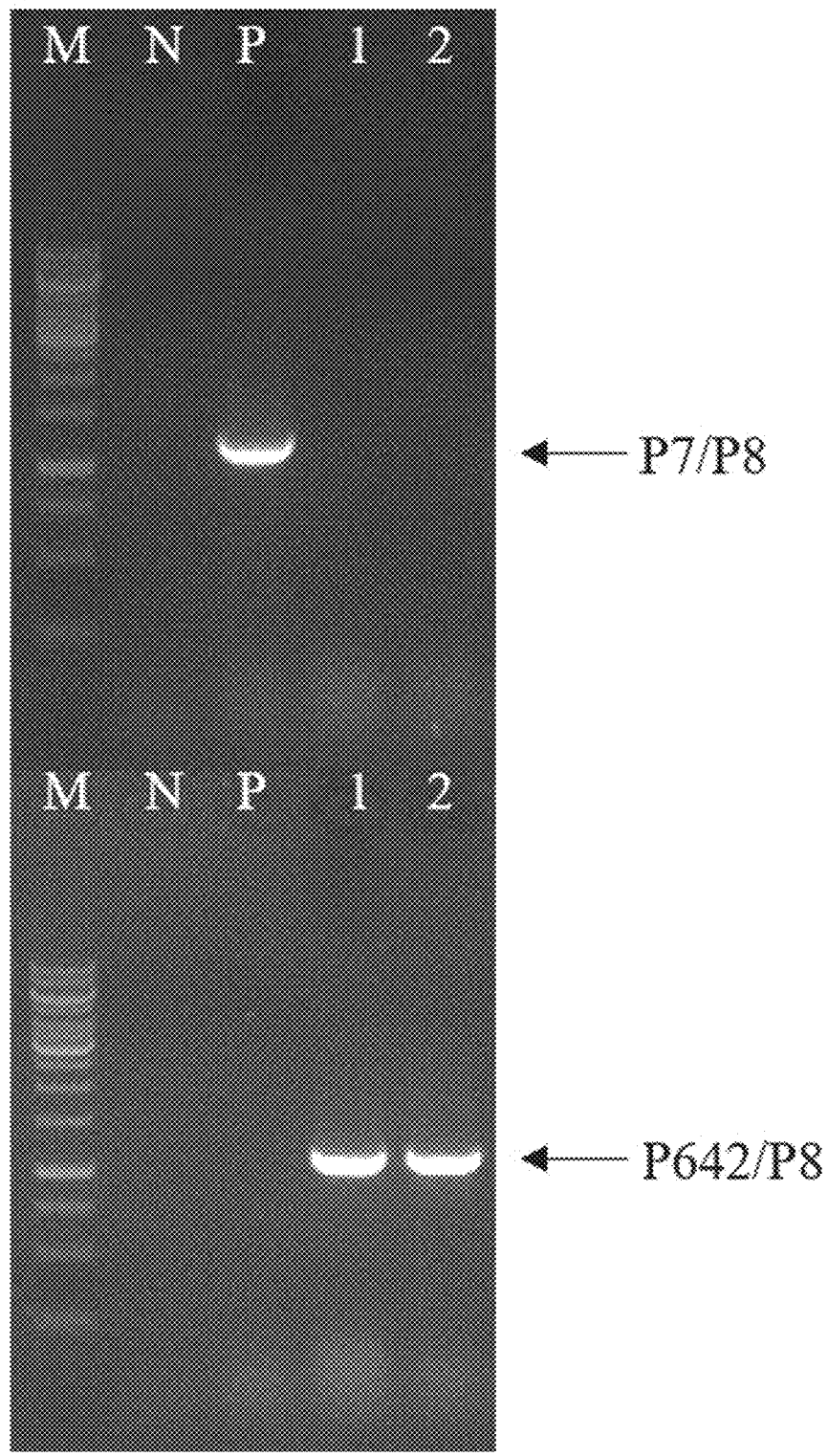
FIG. 15 is a PCR validation diagram of a frdB gene knockout right homology arm in the disclosure, primers P7 and P8 verify a right homology arm, and primers P642 and P8 verify a right homology arm-php; wherein, M is DNA Marker, and N is negative Control, P is a positive control, and 1-2 is the Aspergillus niger transformant genome in which a frdB gene is successfully knocked out.

The vector pLH1162 was electroporated into agrobacterium, and then this agrobacterium and frdA gene knockout strain K1 were co-cultured on an IM medium for agrobacterium-mediated transformation, the culture product was evenly coated in a CM culture medium after culturing for 2.5 days to be cultured until transformants were grown, and then the transformants were transferred to different culture mediums to be screened. The phenotypes of the transformants on different culture mediums should have resistance to hygromycin and sensitivity to glufosinate-ammonium. Such the transformants were subjected to genome validation and validation primers were designed (Table 1). Amplification results satisfy that the amplification of the left and right homology arms is negative (FIG. 14 (P5/P6) FIG. 15 (P7/P8)), and the amplification of the left and right homology arms-php is positive (FIG. 14 (P5/P641) FIG. 15 (P642/P8)), one of the correct frdB knockout clones was picked for induction and recombination of resistance marker hygromycin, so as to obtain a frdB knockout strain K2 without hygromycin resistance.

Example 3: use of an engineered strain in production of L-malic acid via fermentation A method for producing malic acid by utilizing Aspergillus niger frdA gene and frdB gene knockout strains K1 and K2 constructed in the disclosure in a shaker via fermentation specifically comprises the following steps:

First, the obtained engineered strains K1 and K2 were inoculated into a PDA culture medium and subjected to inverted culture in a 28° C. incubator for 5 days until enough conidia were generated;

then, the conidia of strains K1 and K2 were collected and inoculated into a malic acid fermentation culture medium, wherein the final concentration of the conidia was $1*10^8$ conidia/mL, and the shaker was placed under the conditions of 28° C. and at 200 rpm for 5 days of culture.

The malic acid fermentation culture medium comprises the compositions: 100 g/L of glucose, 6 g/L of bacterial peptone, 0.15 g/L of anhydrous potassium dihydrogen phosphate, 0.15 g/L of anhydrous dipotassium hydrogen phosphate, 0.1 g/L of calcium chloride dihydrate, 0.1 g/L of magnesium sulfate heptahydrate, 0.005 g/L of sodium chloride, 0.005 g/L of ferrous sulfate heptahydrate and 0.001 g/L of anhydrous citric acid. Autoclaving was performed for 20 min at 115° C.

Figure 16:
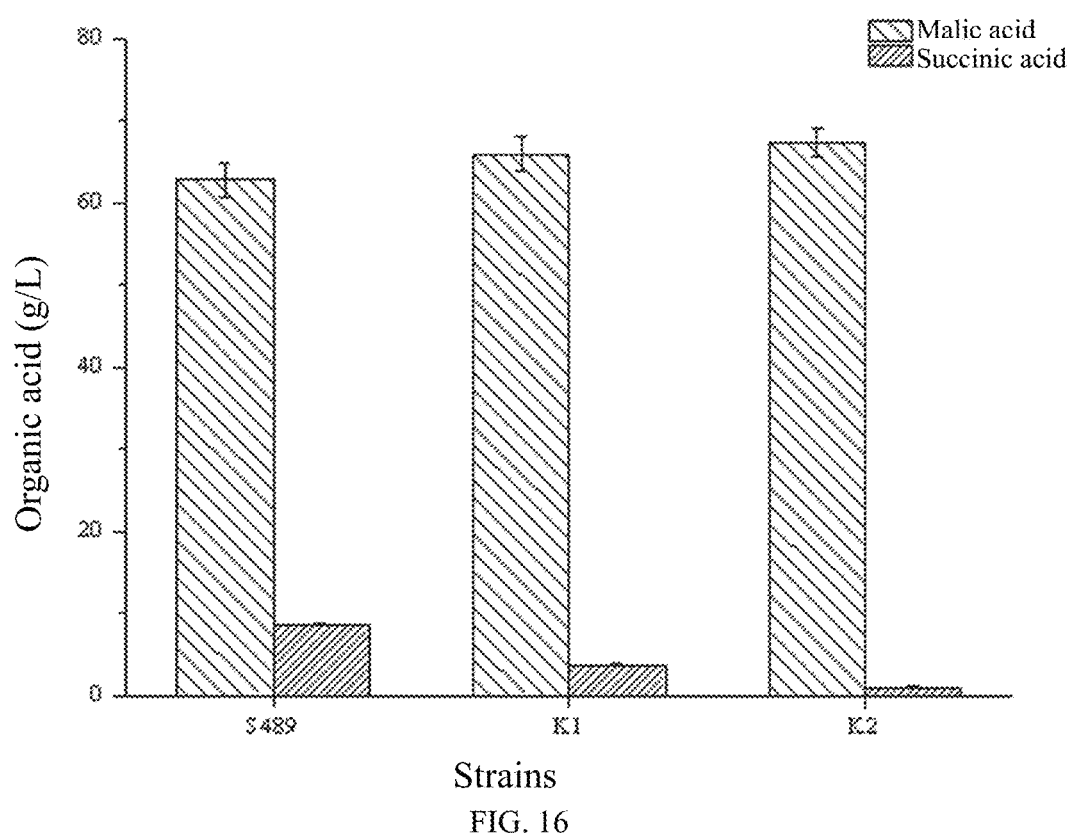
FIG. 16 is a graph showing an organic acid yield of an engineered strain constructed in the disclosure after being fermented in a shaker; S489 is an organic acid yield of a starting strain on day 5, K1 is an organic acid yield of a frdA gene knockout strain on day 5, and K2 is an organic acid yield of a frd A gene and frdB gene double-knockout strain on day 5.

Finally, the fermentation product was collected to prepare a test sample, and the content of the main organic acid in the sample was determined by HPLC. The results showed that the main organic acid was malic acid, the content of the byproduct succinic acid of the frdA gene knockout engineered strain K1 was reduced to 43.07% of a starting strain, while the content of the byproduct succinic acid of the frdA and frdB gene double-knockout strain K2 was reduced by 88.74% compared with that of the starting strain. The results are shown in FIG. 16.

A method for preparing the detection sample comprises: 2 mL of evenly vibrated fermentation broth was sucked, an equal volume of 2 M HCl was added, the above materials fully reacted, the reaction product was centrifuged to take supernatant, the supernatant was diluted by 50 folds, and the diluted supernatant was filtered via a 0.22 μm filter membrane and then stored in a liquid vial for future HPLC analysis.

A method for detecting an organic acid via HPLC comprises: Agilent high performance liquid chromatograph UV detector, AminexHPX-87H chromatographic column (300 mm*7.8 mm), 5 mM $H_2SO_4$ mobile phase, 0.6 mL/min flow rate, the column temperature was 65° C., the detection wavelength was 210 nm, and the injection volume was 20 μL.

According to research results of the disclosure, the byproduct succinic acid accumulated in the production process of malic acid through fermentation of Aspergillus niger is significantly reduced, the cost in the process of downstream separation and purification malic acid was reduced, and good strains are provided for industrialized production of malic acid via fermentation.

Although the embodiments of the disclosure have been disclosed for illustrative purposes, those skilled in the art will appreciate that various substitutions, changes and modifications are possible without departing from the spirit and scope of the disclosure and the appended claims, and therefore the scope of the disclosure is not limited to the contents disclosed in the embodiments.

We claim:

1. A method of constructing an Aspergillus niger engineered strain, wherein the Aspergillus niger engineered strain is capable of reducing the byproduct succinic acid in a fermentation process for making L-malic acid, wherein fumaric acid reductase frdA and fumaric acid reductase flavoprotein subunit frdB are simultaneously knocked out from the Aspergillus niger engineered strain;

wherein the method comprises the following steps:
(1) respectively amplifying upstream and downstream sequence fragments of a gene frdA through PCR with a wild type Aspergillus niger ATCC1015 genome as a template, and recovering PCR products to respectively obtain target fragments; and cloning the upstream and downstream sequence fragments of the gene frdA into a vector pLH594, so as to construct a fumaric acid reductase frdA knockout vector pLH1067;

wherein the downstream sequence of the gene frdA is SEQ NO:3, and the upstream sequence of the gene frdA is SEQ NO: 4; and transferring said vector pLH1067 into Aspergillus niger S489 under the mediation of Agrobacterium, and conducting transformant screening and hygromycin resistance gene recombination to obtain a frdA gene knockout strain K1; and (2) respectively amplifying upstream and downstream sequence fragments of gene frdB through PCR with a wild type Aspergillus niger ATCC1015 strain genome as a template, and recovering PCR products to obtain target sequence fragments; and cloning the upstream and downstream target sequence fragments of the gene frdB into vector pLH594, so as to construct a fumaric acid reductase flavoprotein subunit frdB knockout vector pLH1162;

wherein the downstream sequence of the gene frdB is SEQ NO:7, and the upstream sequence of the gene frdB is SEQ NO: 8; and transferring vector pLH1162 into the frdA gene knockout strain K1 under the mediation of Agrobacterium, and conducting transformant screening and hygromycin resistance gene recombination to obtain a frdA gene and frdB gene double-knockout strain K2, that is the Aspergillus niger engineered strain for reducing the byproduct succinic acid accumulation in the fermentation process for making L-malic acid.

2. The method according to claim 1, wherein the amino acid sequence encoded by the fumaric acid reductase gene frdA is SEQ NO:2, the gene sequence of the fumaric acid reductase flavoprotein subunit gene frdB is SEQ NO:5, and the amino acid sequence encoded by the fumaric acid reductase flavoprotein subunit gene frdB is SEQ NO:6.

3. The method according to claim 1, wherein the gene sequence of the fumaric acid reductase gene frdA is SEQ ID NO: 1, and the gene sequence of the fumaric acid reductase flavoprotein subunit gene frdB is SEQ ID NO: 5.

* * * * *

```
SEQUENCE LISTING

<160> NUMBER OF SEQ ID NOS: 26

<210> SEQ ID NO 1
<211> LENGTH: 2496
<212> TYPE: DNA
<213> ORGANISM: Artificial Sequence
<220> FEATURE:
<223> OTHER INFORMATION: synthesized

<400> SEQUENCE: 1
ccctttaatc tcctcttctc atctctcccc cattcatctt tgaatttctc ttctcatcct        60 tgtctcccctt ccctctacat cttcctccca cacgatggca accgccccta gagtaatcgt      120
tgttggcggt ggacgtgagt tgatcttcac cgccaggaaa cagctttccc cgcattgctg      180
accattgtct cgtctctcag tgtccgggct tagtgccgcc cacaccgtct accttaacgg      240
tggaaatgtt ctcgttctag acaagcaggg tatgtcgaca agccgtagct cccggcgata      300
attgcagtcg catcattatc gttcggtatt atcgtctgga aactaactcc agacagcctt      360
cttcggtggc aactccacca aggccacttc cggcatcaac ggtgccctga cgcgtaccca      420
ggtcgacttg ggcatcgccg acagcgtcaa gcaattttac gatgataccc tcaaatctgc      480
tagagacaag gctcgtcccg agctgatcaa ggtcctcaca tacaagtccg ctgctgccgt      540
```

```
cgagtggttg caggatgttt tcaacctcga tctcacccct gtttcccggc tagggtaagc    600
attgcgcttt aaatgtcact acagcgtctg tcgcgcaacc ttatgctaat tcgtgcagcg    660
gtcactccca gccccgtacg catcgtggcc acgatgccaa gttccctgga atggccatca    720
catacgccct catgcaacgg ttagaagagc tcaccgagtc tgagcccgac cgtgttcaga    780
tcatcaagaa ggctcgtgtg acctccatca acaagtccgg aaacaatgtg acgggagtta    840
cgtacgagta cgatggcgag acgcatactg ctgatggtgt ggtcgttctg ccactggtg     900 gttacgctgc tgacttcggc gatggctctc tcctgaagca gcaccgcccc gacaccttcg    960
gtctgtccag caccaacggc actcacgcca ctggtgatgg tcagaagatg ctgatggaga    1020
tcggtgccaa cggcatcgac atggacaagg ttcaggtgca ccccacaggt ctcgtcgacc    1080
ctaaggaccc gaccgccaaa ttcaagttcc tggctgctga agccctgcgt ggtgagggtg    1140
gtctccttct caactcggac ggccagcggt tctcggatga actgggccac cgtgactacg    1200
tctcgggaca gatgtggaag gagaaggaga agggcaagtg gcccatccgt ctcatcctca    1260
acagcaaggc atccaatgtc ctggacttcc acacccgcca ctactctggc cgtggtctga    1320
tgaagaagat gaccggcaag gagctcgcca aggagatcgg ttgcggcgag cagccctca    1380 agaagacttt cgacgactac aacctgatcg ccgagggcaa gaagaaggac ccttggaaca    1440
agcgtttctt tcacaacctg cccttcagca tcgatgacga cttccacgtg gctctgatgg    1500
agcctgttct gcacttcacc atgggtggta ttgagatcaa cgagcacgcc caggttctca    1560
actccgagaa ggaagccttc gacggcctct acgcttgtgg tgagctggct ggtggtgtcc    1620
acggtgctaa ccgtctgggt ggttcttctc tgctgggttg tgtcgtatac ggtcgcgttg    1680
cgggtgacag cgctagccag tacctcttcc agaagctgct ttccggcggt gcctccacgg    1740
ccgcccagcg actgggccag atctccctgc acatcgaccc gtcaaccccc ggcaagatct    1800
ccgttgaatg gggcggctcc ggcgccgctg gtggccagat cgccgccggt gctgaaccc     1860 cagctgccgc ggcccagggc gccaagtcgg cagccacccc tgccggtgcc gctgagacag    1920
ccaagcccaa ggagcccgcc aagttcagca ttcccgagaa ggaatactcc atggaggaga    1980
tcgccaagca caacaagaag gacgacctgt ggattgtcgt caagggtgtc gtgctggacg    2040
tgaccaactg gctcgatgag caccctggtg gagctaacgc tctcttcaac ttcatgggcc    2100
gcgatgccac agaaggtatg tcttccccaa ctttgtctca tctccagaat atatatatac    2160
taacttcaat ccccaatcac agagttcgca atgctccacg acgacgaggt catccccaag    2220
tacgctggtc acattgtgat cggccgtgtc aagggccaga cccttagcc tagagctgta     2280 aaaaccccgt gaaaatttag aatcggagac atatacgttg gagaagagaa agtaaccagg    2340
aagagatcac atacccatttt tctttatcta tttacctgtt tgttttgtcg agcatgttca    2400
tgtccacgtc cttggtgatg atgagtaggc tcttttatcc ggagtcacta tgtgtctagt    2460
atgtaagata caatcctagt caattgttct tagaca                              2496
```

<210> SEQ ID NO 2
<211> LENGTH: 629
<212> TYPE: PRT
<213> ORGANISM: Artificial sequence
<220> FEATURE:
<223> OTHER INFORMATION: synthesized

<400> SEQUENCE: 2

Met Ala Thr Ala Pro Arg Val Ile Val Val Gly Gly Gly Leu Ser Gly
1               5                   10                  15

```
Leu Ser Ala Ala His Thr Val Tyr Leu Asn Gly Gly Asn Val Leu Val
         20                  25                  30

Leu Asp Lys Gln Ala Phe Phe Gly Asn Ser Thr Lys Ala Thr Ser
         35                  40                  45

Gly Ile Asn Gly Ala Leu Thr Arg Thr Gln Val Asp Leu Gly Ile Ala
 50                  55                  60

Asp Ser Val Lys Gln Phe Tyr Asp Asp Thr Leu Lys Ser Ala Arg Asp
 65                  70                  75                  80

Lys Ala Arg Pro Glu Leu Ile Lys Val Leu Thr Tyr Lys Ser Ala Ala
                 85                  90                  95

Ala Val Glu Trp Leu Gln Asp Val Phe Asn Leu Asp Leu Thr Leu Val
             100                 105                 110

Ser Arg Leu Gly Gly His Ser Gln Pro Arg Thr His Arg Gly His Asp
         115                 120                 125

Ala Lys Phe Pro Gly Met Ala Ile Thr Tyr Ala Leu Met Gln Arg Leu
130                 135                 140

Glu Glu Leu Thr Glu Ser Glu Pro Asp Arg Val Gln Ile Ile Lys Lys
145                 150                 155                 160

Ala Arg Val Thr Ser Ile Asn Lys Ser Gly Asn Asn Val Thr Gly Val
                 165                 170                 175

Thr Tyr Glu Tyr Asp Gly Glu Thr His Thr Ala Asp Gly Val Val Val
             180                 185                 190

Leu Ala Thr Gly Gly Tyr Ala Ala Asp Phe Gly Asp Gly Ser Leu Leu
         195                 200                 205

Lys Gln His Arg Pro Asp Thr Phe Gly Leu Ser Ser Thr Asn Gly Thr
210                 215                 220

His Ala Thr Gly Asp Gly Gln Lys Met Leu Met Glu Ile Gly Ala Asn
225                 230                 235                 240

Gly Ile Asp Met Asp Lys Val Gln Val His Pro Thr Gly Leu Val Asp
                 245                 250                 255

Pro Lys Asp Pro Thr Ala Lys Phe Lys Phe Leu Ala Ala Glu Ala Leu
             260                 265                 270

Arg Gly Glu Gly Gly Leu Leu Leu Asn Ser Asp Gly Gln Arg Phe Ser
         275                 280                 285

Asp Glu Leu Gly His Arg Asp Tyr Val Ser Gly Gln Met Trp Lys Glu
290                 295                 300

Lys Glu Lys Gly Lys Trp Pro Ile Arg Leu Ile Leu Asn Ser Lys Ala
305                 310                 315                 320

Ser Asn Val Leu Asp Phe His Thr Arg His Tyr Ser Gly Arg Gly Leu
                 325                 330                 335

Met Lys Lys Met Thr Gly Lys Glu Leu Ala Lys Glu Ile Gly Cys Gly
             340                 345                 350

Glu Ala Ala Leu Lys Lys Thr Phe Asp Asp Tyr Asn Leu Ile Ala Glu
         355                 360                 365

Gly Lys Lys Lys Asp Pro Trp Asn Lys Arg Phe Phe His Asn Leu Pro
370                 375                 380

Phe Ser Ile Asp Asp Phe His Val Ala Leu Met Glu Pro Val Leu
385                 390                 395                 400

His Phe Thr Met Gly Gly Ile Glu Ile Asn Glu His Ala Gln Val Leu
                 405                 410                 415

Asn Ser Glu Lys Glu Ala Phe Asp Gly Leu Tyr Ala Cys Gly Glu Leu
             420                 425                 430
```

```
Ala Gly Gly Val His Gly Ala Asn Arg Leu Gly Gly Ser Ser Leu Leu
            435                 440                 445
Gly Cys Val Val Tyr Gly Arg Val Ala Gly Asp Ser Ala Ser Gln Tyr
450                 455                 460
Leu Phe Gln Lys Leu Leu Ser Gly Gly Ala Ser Thr Ala Ala Gln Arg
465                 470                 475                 480
Leu Gly Gln Ile Ser Leu His Ile Asp Pro Ser Thr Pro Gly Lys Ile
                485                 490                 495
Ser Val Glu Trp Gly Gly Ser Gly Ala Ala Gly Gln Ile Ala Ala
                500                 505                 510
Gly Ala Gly Thr Pro Ala Ala Ala Gln Gly Ala Lys Ser Ala Ala
            515                 520                 525
Thr Pro Ala Gly Ala Ala Glu Thr Ala Lys Pro Lys Glu Pro Ala Lys
530                 535                 540
Phe Ser Ile Pro Glu Lys Glu Tyr Ser Met Glu Ile Ala Lys His
545                 550                 555                 560
Asn Lys Lys Asp Asp Leu Trp Ile Val Lys Gly Val Val Leu Asp
                565                 570                 575
Val Thr Asn Trp Leu Asp Glu His Pro Gly Gly Ala Asn Ala Leu Phe
                580                 585                 590
Asn Phe Met Gly Arg Asp Ala Thr Glu Glu Phe Ala Met Leu His Asp
            595                 600                 605
Asp Glu Val Ile Pro Lys Tyr Ala Gly His Ile Val Ile Gly Arg Val
            610                 615                 620
Lys Gly Gln Thr Pro
625

<210> SEQ ID NO 3
<211> LENGTH: 1245
<212> TYPE: DNA
<213> ORGANISM: Artificial Sequence
<220> FEATURE:
<223> OTHER INFORMATION: synthesized

<400> SEQUENCE: 3
gcctagagct gtaaaaaccc cgtgaaaatt tagaatcgga gacatatacg ttggagaaga      60
gaaagtaacc aggaagagat cacatacccc a ttttctttat ctatttacct gtttgttttg    120
tcgagcatgt tcatgtccac gtccttggtg atgatgagta ggctctttta tccggagtca    180
ctatgtgtct agtatgtaag atacaatcct agtcaattgt tcttagacat agtcgctgcc    240
agatatgtaa gacttaaagg taaaaatagc agcaaacaat agacagctgc aacgacacca    300
gtaatgaaca gtacatatcc gaaaccagcg aagaaagaaa caatgatgta aatgtatcct    360
agcttcagtg atccaattat ccgatcatta aatacaatt gaacaatatg agtaagccga    420
gtcctcggca agtccgggtc attgctgcat gtgcctcaag atcatcttca gacgtcgcac    480
ggcaggcccc tcttccgtgc ttccggagtc cttattggat ccatttcct ggccgcagc     540 ctctagcgta gggcgaaggt agccccagac ctcgtcatgg tatcggtcct cgacactaag    600
ccagtccgct gcgcccggga gaccggtcag gacggtttcc cgcagggtgg ctacgtctga    660
atggccttgt gatggaacgg tgtctaggaa ttcgccaatg tctgggacca gactgtggga    720
tgtcaatgta ttattgtcgt gtgagggcag cgctgtggac gatgttgggg gtgtaagacg    780
acggaaggac tcgatcattt cctttctttc gggtgtgagt tgcattggaa gcagctctgt    840
ttcgactatg tcggcgggct cgtcggccgt gggagggaat tcgggatcga agctctgatc    900
```

| | |
|---|---|
| agagaggagg gatacgactg cgtcaccgtc ggatgggagg agagagggtc ggtcgggttg | 960 |
| gaacctttgt tcggttgaaa ctggattagt atagtcgccg gagagcaaat ccgttgcagt | 1020 |
| atctctccct ttcccttcc ctttgcccgt agattcgtcc gcgtttagac ctgcaatgaa | 1080 |
| gctgtcattg tttccgacca gggattccgc gccgtaagtg cgttggaatt catcttccga | 1140 |
| gagtggaggg agctggaacc ctccctgttg cacggtggta gctgagcgaa atgcttcagc | 1200 |
| aggggcaggt agtgaagaat cccagtcga gggagaggca gaagt | 1245 |

```
<210> SEQ ID NO 4
<211> LENGTH: 1285
<212> TYPE: DNA
<213> ORGANISM: Artificial Sequence
<220> FEATURE:
<223> OTHER INFORMATION: synthesized

<400> SEQUENCE: 4
```

| | |
|---|---|
| caggtgacgt gggaaggatc ggttgttggg gggatttggt atgtacgttt tgtatttatg | 60 |
| tattgtatgc tggggcttta ttgttttcag tatggtttgt tgttgacgtt ttgaatgtgt | 120 |
| gtcttcaagg atttaattta gttagtggcg ttgtagtgag ttgaggtatg ggctgatttt | 180 |
| gttcaaggtg atcggtgatg atgatgggt ctcggtccga ggtaagtgat cgaggcctgg | 240 |
| ggggggggta ttggatgtat tgaagttttg ttgccattct tcaaggtccc tgtctttgtg | 300 |
| tgtatgtatg tatggggtaa ttcggatact taaataaggt gtattgaata ctaattatga | 360 |
| tagttcttat tgatagtgtt tgtgtttgtt gttgtagtga atgtatatat atataatgtg | 420 |
| agatcaacca gttccaggta ctatctaagc ttcagatgaa aagctacctt cacttcacta | 480 |
| aatagacatc tcattcatga aatctagatg gagcagacat cccgatcatc taggtaaccc | 540 |
| caaaattgag acgaatctga atccggggac agagtttaaa tcgaagagca tgacgtgccg | 600 |
| cgctgactta agcctacgat ttcatttgct gaaaggctgc tgctgggtt tccaggcatg | 660 |
| tgaaagcctg ggagtctctc tcttgccctc aggtatgctt gtagtataat atgtcatggg | 720 |
| aaggaaccgc agggtcagct tgcagctcct ggtgacgctc tgcatgtgat ggaccctgg | 780 |
| tctgctggaa actcactagt attctgtcaa cgacagggga gtgattttg aatgtctact | 840 |
| gcctattgat aactcgactg tagtacctat actaagtaga acccgtcatt cagtcagtca | 900 |
| agaagcacag gccagagaca gacaaaagaa ggacccatcg aatccactta agacaggctg | 960 |
| aacattcgtt gatcccctca aaaagtagaa gagaagatac cggaccggaa aagggagagg | 1020 |
| agggaggagg gggtcataga acggtaatcg tacggtacat acccgagttg aatgaattga | 1080 |
| atggggaaga aatgagcctc ggccgagtga gtgagtctct ccccgtcgg cttctgaatg | 1140 |
| cctggctcta ctcttcttcc cccggatctc ctggtgctta aagatctact tgttcctacc | 1200 |
| tgcttttga cccctttaatc tcctcttctc atctctcccc cattcatctt tgaatttctc | 1260 |
| ttctcatcct tgtctccctt ccctc | 1285 |

```
<210> SEQ ID NO 5
<211> LENGTH: 1569
<212> TYPE: DNA
<213> ORGANISM: Artificial Sequence
<220> FEATURE:
<223> OTHER INFORMATION: synthesized

<400> SEQUENCE: 5
```

| | |
|---|---|
| atggctcttc cctcagaatg cgacgtgctc gtcattggcg gcgggaatgc cggcttctgc | 60 |
| gcagccattt cggcagtcca gtccggcgca aaacacgttg ctatcatcga taatgtccg | 120 |

-continued

```
gaggaatggg caggaggtaa ctcttacttc acagcggggg caatgcgcac cgtccacggc    180
ggattgccgg atctgcttcc catcgtgaat aatgtcgatg cggagacggc gaagaagatt    240
gatatgaagc cgtataccgt ggaggacttc accggcgaca tgaaccgtgt tacggggcgg    300
cgcaccaacc gcgagctctg ccagacactc gtcaatgagt caaactcggc gatcaagtgg    360
ctggctagta atggcgtgcg cttccagctc tctttcaatc gacaggcgta tgaagtcaac    420
ggccgcctca agttctgggg tggtcttgcg ctgaagactc aagatggcgg caagggtctc    480
attcaggatc acctgcaagc agcccggaaa ctgggcatta aggtggtctt ctcgaccgct    540
gctcagaaac tagtaacgga tccggtctct ggagccgtga cgtccgtcgt ggtttcgcat    600
cacggccgcg agcagactgt taaggctggg gccgtgattc tcgcggccgg aggcttcgaa    660
gggaacccgc gcatgcgcgc gcagtacctt ggaccacact gggacgtggc gctggtacgc    720
ggcacgccct ataactctgg ggatggattc gagatggcga tccgggatgt ctcagccaag    780
caggcgggca actggtcagg atgtcactgc gtggcgtggg atgctaacgc accggccgat    840
acgggcgacc gggagatctc caacgagttc accaagtccg ggtatccgtt gggcatcatg    900
atcaatcggc agggaaaccg gttcgtggac gaggggtcgg atctgcgcaa ctatacgtat    960
gcgatgatcg gacgccagat tctcaaccag cccggccaca tggcgttcca gatctgggac    1020
tccaagatga tcccttggtt gcggtcggag gagtaccggc cggaggtagt gcagcatatc    1080
agcgcggcca cgatcagtga gctggcggag aagtgtgccg agtttgatct cgaggataag    1140
aagcgctttg agcagaccat ccatgactat aataaggcgg tttatgagcg ccagcgcagg    1200
catccgggtg ggaagtggga tccggctgtc aaagatggac ttaccacgca gtcggagggc    1260
ttggagctgg cagttcccaa gtcgaactgg gcgcttccta ttgatcaagg accgttcctg    1320
gctgtccggg tcacggcggg catcactttt acgtttggtg gactggcggt tcgtccggag    1380
acggcggcgg tggtgtcgtc gacaacaaac caagaggtgc cggggttgta ctgcgcaggg    1440
gagatgctgg gaggactgtt ttatgacaac tatcctggag gcagtggatt gacgtcgggg    1500
gctgtctttg gacgacgagc tggtcgggct gcggcggcga gggtgtcgag ccggcaggca    1560
cggttgtag                                                            1569
```

<210> SEQ ID NO 6
<211> LENGTH: 522
<212> TYPE: PRT
<213> ORGANISM: Artificial Sequence
<220> FEATURE:
<223> OTHER INFORMATION: synthesized

<400> SEQUENCE: 6

```
Met Ala Leu Pro Ser Glu Cys Asp Val Leu Val Ile Gly Gly Gly Asn
1               5                   10                  15

Ala Gly Phe Cys Ala Ala Ile Ser Ala Val Gln Ser Gly Ala Lys His
            20                  25                  30

Val Ala Ile Ile Asp Lys Cys Pro Glu Glu Trp Ala Gly Gly Asn Ser
        35                  40                  45

Tyr Phe Thr Ala Gly Ala Met Arg Thr Val His Gly Gly Leu Pro Asp
    50                  55                  60

Leu Leu Pro Ile Val Asn Asn Val Asp Ala Glu Thr Ala Lys Lys Ile
65                  70                  75                  80

Asp Met Lys Pro Tyr Thr Val Glu Asp Phe Thr Gly Asp Met Asn Arg
                85                  90                  95
```

-continued

```
Val Thr Gly Arg Arg Thr Asn Arg Glu Leu Cys Gln Thr Leu Val Asn
            100                 105                 110

Glu Ser Asn Ser Ala Ile Lys Trp Leu Ala Ser Asn Gly Val Arg Phe
        115                 120                 125

Gln Leu Ser Phe Asn Arg Gln Ala Tyr Glu Val Asn Gly Arg Leu Lys
    130                 135                 140

Phe Trp Gly Gly Leu Ala Leu Lys Thr Gln Asp Gly Gly Lys Gly Leu
145                 150                 155                 160

Ile Gln Asp His Leu Gln Ala Ala Arg Lys Leu Gly Ile Lys Val Val
                165                 170                 175

Phe Ser Thr Ala Ala Gln Lys Leu Val Thr Asp Pro Val Ser Gly Ala
            180                 185                 190

Val Thr Ser Val Val Val Ser His His Gly Arg Glu Gln Thr Val Lys
        195                 200                 205

Ala Gly Ala Val Ile Leu Ala Ala Gly Gly Phe Glu Gly Asn Pro Arg
    210                 215                 220

Met Arg Ala Gln Tyr Leu Gly Pro His Trp Asp Val Ala Leu Val Arg
225                 230                 235                 240

Gly Thr Pro Tyr Asn Ser Gly Asp Gly Phe Glu Met Ala Ile Arg Asp
                245                 250                 255

Val Ser Ala Lys Gln Ala Gly Asn Trp Ser Gly Cys His Cys Val Ala
            260                 265                 270

Trp Asp Ala Asn Ala Pro Ala Asp Thr Gly Asp Arg Glu Ile Ser Asn
        275                 280                 285

Glu Phe Thr Lys Ser Gly Tyr Pro Leu Gly Ile Met Ile Asn Arg Gln
    290                 295                 300

Gly Asn Arg Phe Val Asp Glu Gly Ser Asp Leu Arg Asn Tyr Thr Tyr
305                 310                 315                 320

Ala Met Ile Gly Arg Gln Ile Leu Asn Gln Pro Gly His Met Ala Phe
                325                 330                 335

Gln Ile Trp Asp Ser Lys Met Ile Pro Trp Leu Arg Ser Glu Glu Tyr
            340                 345                 350

Arg Pro Glu Val Val Gln His Ile Ser Ala Ala Thr Ile Ser Glu Leu
        355                 360                 365

Ala Glu Lys Cys Ala Glu Phe Asp Leu Glu Asp Lys Lys Arg Phe Glu
    370                 375                 380

Gln Thr Ile His Asp Tyr Asn Lys Ala Val Tyr Glu Arg Gln Arg Arg
385                 390                 395                 400

His Pro Gly Gly Lys Trp Asp Pro Ala Val Lys Asp Gly Leu Thr Thr
                405                 410                 415

Gln Ser Glu Gly Leu Glu Leu Ala Val Pro Lys Ser Asn Trp Ala Leu
            420                 425                 430

Pro Ile Asp Gln Gly Pro Phe Leu Ala Val Arg Val Thr Ala Gly Ile
        435                 440                 445

Thr Phe Thr Phe Gly Gly Leu Ala Val Arg Pro Glu Thr Ala Ala Val
    450                 455                 460

Val Ser Ser Thr Thr Asn Gln Glu Val Pro Gly Leu Tyr Cys Ala Gly
465                 470                 475                 480

Glu Met Leu Gly Gly Leu Phe Tyr Asp Asn Tyr Pro Gly Gly Ser Gly
                485                 490                 495

Leu Thr Ser Gly Ala Val Phe Gly Arg Arg Ala Gly Arg Ala Ala Ala
            500                 505                 510

Ala Arg Val Ser Ser Arg Gln Ala Arg Leu
```

```
                            515                     520
```

<210> SEQ ID NO 7
<211> LENGTH: 881
<212> TYPE: DNA
<213> ORGANISM: Artificial Sequence
<220> FEATURE:
<223> OTHER INFORMATION: synthesized

<400> SEQUENCE: 7

```
gaccacactg ggacgtggcg ctggtacgcg gcacgcccta taactctggg gatggattcg      60
agatggcgat ccgggatgtc tcagccaagc aggcgggcaa ctggtcagga tgtcactgcg     120
tggcgtggga tgctaacgca ccggccgata cgggcgaccg ggagatctcc aacgagttca     180
ccaagtccgg gtatccgttg gcatcatga tcaatcggca gggaaaccgg ttcgtggacg      240
aggggtcgga tctgcgcaac tatacgtatg cgatgatcgg acgccagatt ctcaaccagc     300
ccggccacat ggcgttccag atctgggact ccaagatgat cccttggttg cggtcggagg     360
agtaccggcc ggaggtagtg cagcatatca gcgcggccac gatcagtgag ctggcggaga     420
agtgtgccga gtttgatctc gaggataaga agcgctttga gcagaccatc catgactata     480
ataaggcggt ttatgagcgc cagcgcaggc atccgggtgg gaagtgggat ccggctgtca     540
aagatggact taccacgcag tcggagggct tggagctggc agttcccaag tcgaactggg     600
cgcttcctat tgatcaagga ccgttcctgg ctgtccgggt cacggcgggc atcacttttta    660
cgtttggtgg actggcggtt cgtccggaga cggcggcggt ggtgtcgtcg acaacaaacc     720
aagaggtgcc ggggttgtac tgcgcagggg agatgctggg aggactgttt tatgacaact     780
atcctggagg cagtggattg acgtcggggg ctgtctttgg acgacgagct ggtcgggctg     840
cggcggcgag ggtgtcgagc cggcaggcac ggttgtagtc t                         881
```

<210> SEQ ID NO 8
<211> LENGTH: 1463
<212> TYPE: DNA
<213> ORGANISM: Artificial Sequence
<220> FEATURE:
<223> OTHER INFORMATION: synthesized

<400> SEQUENCE: 8

```
gtgcaccttt caccgtcctg ccggccctga tgaacgaata ccgtgtgccc gaactgaacg      60
tccagaacgg tgtgctcaag gccatgtcct tcttgttcga gtacattggc gagatggcca     120
aggattacgt ctacgcagtc acgcctcttc tggaggatgc tctcatcgat cgcgaccagg     180
tgcaccggca gaccgcagcc agcgttgtca agcacatcgc gctgggcgtg gttggtttgg     240
gatgtgaaga cgcaatggtg catctgctta acctggtgtt ccccaacatc ttcgagacca     300
gcccccacgt catcgaccgt gtcattgaag ccattgatgc gatccggatg gcagtcggca     360
ccggtgtggt catgaactac gtgtgggcag gcttgttcca ccggcgcgc aaggtgcgca     420
cgccgtattg gcgactgtac aacgatgcgt acgtgcagag tgcggacgcg atgattccct     480
actaccccgg cctggaagac gatggtctgg accggactga gttgtctatc atagtttgaa     540
caaaagccag ccagcgcgtg tcatttatca tcatcttctt ctctgtctct gtaccctctt     600
ctgccgtgtg ttttttctatc ttctcaacat attggggctt gttcaattac ggtgtttctc     660
tggcgggatt tggcgtgtct gaaccatctt tatctaagat atagtagtct atggcaatat     720
ccaacatttc aacgttcaat ataattctat cccatttact ttccgttcgg cacttctgta     780
agtcaaacta gtactcaact gattgatcga agcgatcgat cttttccattc ccgatcgacc     840
```

```
ctcgactatt ctctcccccg caatttgcag cgtggggagc acccgcactc acactccgcg    900
catcatgcca tgcatgcgtt cgtttgcgag atccgagtca ccctcgatcg ctctagcaga    960
gctatccact tttctcccta acattcctgt cctacttccg atgacatcaa gcagcgctgc   1020
ccagaccgac cggaaagact ctctccgcct ccctccgtgg caccgacgga cataactct    1080 ccgtttccca accccattcc cccatcctcg gcaccatccc cgccgtccgt cgctacatac   1140
aaagccgcag gcaacttgag cacagatccc agagcactat gtatctactt gatgcgatga   1200
tcatcagtct ccttcccctta gcagactaaa tgcactaatg ctctttctc tttgacgcat    1260 acacgcacgc acgcacgcac aggcacaccc acccacacac acagacacat cactctagca   1320
tcatggctct tccctcagaa tgcgacgtgc tcgtcattgg cggcgggaat gccggcttct   1380
gcgcagccat ttcggcagtc cagtccggcg caaaacacgt tgctatcatc gataaatgtc   1440
cggaggaatg ggcaggaggt aac                                           1463
```

<210> SEQ ID NO 9
<211> LENGTH: 41
<212> TYPE: DNA
<213> ORGANISM: Artificial Sequence
<220> FEATURE:
<223> OTHER INFORMATION: synthesized

<400> SEQUENCE: 9

```
cccagaattc aattcgagct ccaggtgacg tgggaaggat c                         41
```

<210> SEQ ID NO 10
<211> LENGTH: 42
<212> TYPE: DNA
<213> ORGANISM: Artificial Sequence
<220> FEATURE:
<223> OTHER INFORMATION: synthesized

<400> SEQUENCE: 10

```
attatacgaa gttatggatc cgagggaagg gagacaagga tg                        42
```

<210> SEQ ID NO 11
<211> LENGTH: 43
<212> TYPE: DNA
<213> ORGANISM: Artificial Sequence
<220> FEATURE:
<223> OTHER INFORMATION: synthesized

<400> SEQUENCE: 11

```
gctatacgaa gttattctag agcctagagc tgtaaaaacc ccg                       43
```

<210> SEQ ID NO 12
<211> LENGTH: 41
<212> TYPE: DNA
<213> ORGANISM: Artificial Sequence
<220> FEATURE:
<223> OTHER INFORMATION: synthesized

<400> SEQUENCE: 12

```
tgcctgcagg ggcccactag tacttctgcc tctccctcga c                         41
```

<210> SEQ ID NO 13
<211> LENGTH: 41
<212> TYPE: DNA
<213> ORGANISM: Artificial Sequence
<220> FEATURE:
<223> OTHER INFORMATION: synthesized

<400> SEQUENCE: 13
gctccgtaac acccagaatt cgtgcacctt tcaccgtcct g    41

<210> SEQ ID NO 14
<211> LENGTH: 43
<212> TYPE: DNA
<213> ORGANISM: Artificial Sequence
<220> FEATURE:
<223> OTHER INFORMATION: synthesized

<400> SEQUENCE: 14
cgaagttatg gatccgagct cgttacctcc tgcccattcc tcc    43

<210> SEQ ID NO 15
<211> LENGTH: 39
<212> TYPE: DNA
<213> ORGANISM: Artificial Sequence
<220> FEATURE:
<223> OTHER INFORMATION: synthesized

<400> SEQUENCE: 15
gctatacgaa gttattctag agaccacact gggacgtgg    39

<210> SEQ ID NO 16
<211> LENGTH: 40
<212> TYPE: DNA
<213> ORGANISM: Artificial Sequence
<220> FEATURE:
<223> OTHER INFORMATION: synthesized

<400> SEQUENCE: 16
tgcctgcagg ggcccactag tagactacaa ccgtgcctgc    40

<210> SEQ ID NO 17
<211> LENGTH: 19
<212> TYPE: DNA
<213> ORGANISM: Artificial Sequence
<220> FEATURE:
<223> OTHER INFORMATION: synthesized

<400> SEQUENCE: 17
cacggcatgc taattggtg    19

<210> SEQ ID NO 18
<211> LENGTH: 19
<212> TYPE: DNA
<213> ORGANISM: Artificial Sequence
<220> FEATURE:
<223> OTHER INFORMATION: synthesized

<400> SEQUENCE: 18
gatcaactca cgtccaccg    19

<210> SEQ ID NO 19
<211> LENGTH: 20
<212> TYPE: DNA
<213> ORGANISM: Artificial Sequence
<220> FEATURE:
<223> OTHER INFORMATION: synthesized

<400> SEQUENCE: 19
gcgatgccac agaaggtatg    20

<210> SEQ ID NO 20
<211> LENGTH: 19

-continued

<212> TYPE: DNA
<213> ORGANISM: Artificial Sequence
<220> FEATURE:
<223> OTHER INFORMATION: synthesized

<400> SEQUENCE: 20
tcgggccttg caaagaatg                                            19

<210> SEQ ID NO 21
<211> LENGTH: 19
<212> TYPE: DNA
<213> ORGANISM: Artificial Sequence
<220> FEATURE:
<223> OTHER INFORMATION: synthesized

<400> SEQUENCE: 21
ccaggatgtg ttggcgacg                                            19

<210> SEQ ID NO 22
<211> LENGTH: 18
<212> TYPE: DNA
<213> ORGANISM: Artificial Sequence
<220> FEATURE:
<223> OTHER INFORMATION: synthesized

<400> SEQUENCE: 22
tggacggtgc gcattgcc                                             18

<210> SEQ ID NO 23
<211> LENGTH: 18
<212> TYPE: DNA
<213> ORGANISM: Artificial Sequence
<220> FEATURE:
<223> OTHER INFORMATION: synthesized

<400> SEQUENCE: 23
gaacccgcgc atgcgcgc                                             18

<210> SEQ ID NO 24
<211> LENGTH: 21
<212> TYPE: DNA
<213> ORGANISM: Artificial Sequence
<220> FEATURE:
<223> OTHER INFORMATION: synthesized

<400> SEQUENCE: 24
gacatagtat attattcctg c                                         21

<210> SEQ ID NO 25
<211> LENGTH: 20
<212> TYPE: DNA
<213> ORGANISM: Artificial Sequence
<220> FEATURE:
<223> OTHER INFORMATION: synthesized

<400> SEQUENCE: 25
caatatcagt taacgtcgac                                           20

<210> SEQ ID NO 26
<211> LENGTH: 20
<212> TYPE: DNA
<213> ORGANISM: Artificial Sequence

```
<220> FEATURE:
<223> OTHER INFORMATION: synthesized

<400> SEQUENCE: 26
ggaaccagtt aacgtcgaat                                                  20
```